United States Patent
Lewis (10) Patent No.: US 12,357,638 B2
(45) Date of Patent: Jul. 15, 2025

(54) IMMUNOPROTEASOME INHIBITOR FORMULATIONS

(71) Applicant: KEZAR LIFE SCIENCES, South San Francisco, CA (US)

(72) Inventor: Evan Lewis, Pacifica, CA (US)

(73) Assignee: KEZAR LIFE SCIENCES, INC., South San Francisco, CA (US)

( * ) Notice: Subject to any disclaimer, the term of this patent is extended or adjusted under 35 U.S.C. 154(b) by 1074 days.

(21) Appl. No.: 17/281,404

(22) PCT Filed: Oct. 4, 2019

(86) PCT No.: PCT/US2019/054605
§ 371 (c)(1),
(2) Date: Mar. 30, 2021

(87) PCT Pub. No.: WO2020/072848
PCT Pub. Date: Apr. 9, 2020

(65) Prior Publication Data
US 2022/0040192 A1 Feb. 10, 2022

Related U.S. Application Data

(60) Provisional application No. 62/741,221, filed on Oct. 4, 2018.

(51) Int. Cl.
*A61K 31/5377* (2006.01)
*A61K 47/12* (2006.01)
*A61K 47/26* (2006.01)

(52) U.S. Cl.
CPC .......... *A61K 31/5377* (2013.01); *A61K 47/12* (2013.01); *A61K 47/26* (2013.01)

(58) Field of Classification Search
CPC ..... A61K 31/5377; A61K 47/12; A61K 47/26
See application file for complete search history.

(56) References Cited

FOREIGN PATENT DOCUMENTS

| WO | WO-2014/152134 A1 | 9/2014 |
|---|---|---|
| WO | WO-2016/050355 A1 | 4/2016 |
| WO | WO-2018/005772 A1 | 1/2018 |

OTHER PUBLICATIONS

Lickliter et al., KZR-616, a Selective Inhibitor of the Immunoproteasome, Shows a Promising Safety and Target Inhibition Profile in a Phase I, Double-Blind, Single (SAD) and Multiple Ascending Dose (MAD) Study in Healthy Volunteers, 2017 ACR/ARHP Annual Meeting, Arthritis Rheumatol. 2017; 69 (suppl 10):Abstract No. 2587 (2017).
Lickliter et al., AB0509 Kzr-616, a selective inhibitor of the immunoproteasome, shows a promising safety and target inhibition profile in a phase i, double-blind, single (SAD) and multiple ascending dose (MAD) study in healthy volunteers, Annals of the Rheumatic Diseases 2018;77:1413-1414.
International Application No. PCT/US2019/054605, International Search Report and Written Opinion, mailed Feb. 10, 2020.
Muchamuel, J.L. et al. "FRI0296 Kzr-616, a selective inhibitor of the immunoproteasome, blocks the disease progression in multiple models of systemic lupus erythematosus (SLE)". Scientific Abstracts, p. 685 (Jun. 15, 2018).

*Primary Examiner* — Kamal A Saeed
(74) *Attorney, Agent, or Firm* — MARSHALL, GERSTEIN & BORUN LLP (57) ABSTRACT

Provided herein are pharmaceutical formulations comprising KZR-616 or a salt thereof, and a sugar, wherein the formulations are lyophilized, methods of preparing said formulations, methods of treating immune-related diseases, and methods of treating inflammation.

16 Claims, 3 Drawing Sheets

IMMUNOPROTEASOME INHIBITOR FORMULATIONS

BACKGROUND

The compound, (2S,3R)—N-[(2S)-3-(cyclopent-1-en-1-yl)-1-[(2R)-2-methyloxiran-2-yl]-1-oxopropan-2-yl]-3-hydroxy-3-(4-methoxyphenyl)-2-[(2S)-2-[2-(morpholin-4-yl)acetamido]propanamido]propanamide ("KZR-616"), is useful as an immunoproteasome inhibitor:

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

PCT publication no. WO 2014/152134 describes tripeptide epoxyketone proteasome inhibitors and methods of using these compounds to treat diseases and conditions associated with aberrant immunoproteasome activity. Because tripeptide epoxyketone proteasome inhibitors, such as KZR-616, are useful in treating diseases and conditions in a patient, there is a need for soluble and stable formulations of KZR-616.

SUMMARY

Provided herein are pharmaceutical formulations comprising KZR-616 or a salt thereof, and a sugar, wherein KZR-616 has a structure and the formulation is a lyophilized formulation. In some embodiments, the KZR-616 is a maleate salt. In some cases, the formulations have a pH of 3.0 to 4.5, as measured prior to lyophilization. In some cases, the formulations have a pH of 3.8 to 4.3. In some cases, the formulations have a pH of 4.2. In embodiments, the formulations are absent a buffer. In embodiments, the KZR-616 or salt thereof is present at an amount of 50 to 300 mg/mL, as measured prior to lyophilization. In embodiments, the KZR-616 or salt thereof is present at an amount of 100 mg/mL to 200 mg/mL. In some cases, the KZR-616 or a salt thereof is present in an amount of 125 mg/mL based on the weight of the KZR-616 free base.

In some cases, the sugar is present at an amount of 0.1 wt % to 5 wt %, based upon total weight of the formulation. In embodiments, the sugar is present in an amount of 1.5 wt % to 3 wt %. In embodiments, the sugar is present in an amount of 2 wt %. In embodiments, the sugar comprises mannitol, trehalose, or a combination thereof. In some cases, the sugar comprises trehalose.

In embodiments, the lyophilized formulation has a moisture content of less than 1%. In some cases, the formulations have a pH of 4.1 to 4.3 (as measured when reconstituted) after storage at 5° C., 25° C., or 40° C. for at least six months. In embodiments, the formulations have a concentration of KZR-616 or salt thereof of 140 mg/mL to 150 mg/mL (as measured when reconstituted) after storage at 5° C., 25° C., or 40° C. for at least six months. In some cases, the formulations have a reconstituted time of less than 4.5 minutes after storage at 5° C., 25° C., or 40° C. for at least six months. In embodiments, the lyophilized formulations have a moisture content of less than 1% after storage at 5° C., 25° C., or 40° C. for at least six months. In some cases the KZR-616 or a salt thereof is at least 93% pure after storage at 5° C., 25° C., or 40° C. for at least six months.

Also provided herein is a reconstituted formulation comprising the formulations disclosed herein and a solvent for reconstitution. In embodiments, the solvent for reconstitution comprises water for injection (WFI) or aqueous 5% dextrose. In embodiments, the reconstituted formulations have an osmolality of 275 to 325 mOsm. In embodiments, the reconstituted formulations for subcutaneous injection.

In some cases, the reconstituted formulation has an absorption rate, as measured by $T_{1/2}$, of at least 50% faster than that of a formulation comprising KZR-616 or salt thereof and polysorbate-80 ("PS-80 formulation"). In embodiments, the reconstituted formulation has a $C_{max}$ of at least 150% that of a formulation comprising KZR-616 or a salt thereof and polysorbate-80.

Also provided herein is a method for preparing the formulations described herein, comprising admixing KZR-616 or a salt thereof and the sugar to form an aqueous solution, and lyophilizing the aqueous solution to form the lyophilized formulation. In some cases, the method further comprises reconstituting the lyophilized formulation with a solvent to form a reconstituted formulation. In embodiments, the solvent is water for injection or aqueous 5% dextrose. Further provided herein is a method of treating an immune-related disease in a subject comprising administering the reconstituted formulations herein. In some cases, the subject suffers from lupus nephritis or systemic lupus erythematosus (SLE). Also provided herein is a method of treating inflammation in a subject by administering the reconstituted formulations described herein.

DETAILED DESCRIPTION

Provided herein are formulations of KZR-616, or a salt thereof, that are lyophilized and stable. The lyophilized formulations provide benefits, including one or more of a longer shelf life, facile storage at refrigerated temperature, and reduced weight and/or volume of the formulation for shipping and handling. Also disclosed are reconstituted formulations of the lyophilized formulations, methods of preparing the formulations, and methods of treating immune-related diseases and/or inflammation using disclosed formulations.

As further described below, the pharmaceutical formulations of KZR-616 or a salt thereof herein can have several advantages, for example, the formulations disclosed herein can be resistant to changes in pH, concentration, reconstitution time, moisture content, and/or purity after storage at various temperatures and/or time, such as after storage at 5° C., 25° C., or 40° C. for at least six months.

The formulations, dosage presentations, and methods are contemplated to include embodiments including any combination of one or more of the additional optional elements, features, and steps further described below (including those shown in the Tables), unless stated otherwise.

As used herein, the term "treating" or "treatment" includes reversing, reducing, or arresting the symptoms, clinical signs, and underlying pathology of a condition in manner to improve or stabilize a patient's condition.

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

As used herein, the terms "about" and "approximately" generally mean plus or minus 10% of the stated value. For example, about 0.5 would include 0.45 and 0.55, about 10 would include 9 to 11, about 1000 would include 900 to 1100.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of KZR-616 used in formulations herein are within the scope of the invention.

Lyophilized Formulation

Provided herein are pharmaceutical formulations comprising KZR-616 or a salt thereof, and a sugar, wherein KZR-616 has a structure and wherein the formulation is a lyophilized formulation.

The pharmaceutical formulation disclosed herein can comprise KZR-616 in any suitable form. In embodiments, the KZR-616 is present as a free base. In embodiments, the KZR-616 is present as a salt. In some cases, the KZR-616 is present as a salt form selected from maleate, fumarate, oxalate, malate, sulfate, methanesulfonate, 2-naphthalene-sulfonate, phosphate, halide, tartrate, citrate, tosylate, propionate, benzoate, and a combination thereof. In some cases, the KZR-616 is present as a solvate, such as a hydrate. In embodiments, KZR-616 is present as a maleate salt, e.g., a monomaleate salt. In some embodiments, the KZR-616 is present as a dimer salt, e.g., bis(KZR-616) monomaleate.

The formulations described herein can comprise any concentration of KZR-616 or salt thereof, as measured prior to lyophilization. Specifically contemplated concentrations of KZR-616 or salt thereof include about 10 mg/mL to about 500 mg/mL, or about 25 mg/mL to about 400 mg/mL, or about 50 mg/mL to about 400 mg/mL, or about 50 mg/mL to about 300 mg/mL, or about 60 mg/mL to about 275 mg/mL, or about 70 mg/mL to about 250 mg/mL, or about 80 mg/mL to about 225 mg/mL, or about 90 mg/mL to about 225 mg/mL, or about 100 mg/mL to about 200 mg/mL, or about 110 mg/mL to about 200 mg/mL, or about 120 mg/mL to about 200 mg/mL, or about 120 mg/mL to about 220 mg/mL, or about 120 mg/mL to about 190 mg/mL, or about 120 mg/mL to about 180 mg/mL, or about 120 mg/mL to about 170 mg/mL, or about 120 mg/mL to about 160 mg/mL, or about 120 mg/mL to about 150 mg/mL, or about 130 mg/mL to about 150 mg/mL, or about 140 mg/mL to about 150 mg/mL, or about 100 mg/mL to about 150 mg/mL, or about 100 mg/mL to about 140 mg/mL, or about 100 mg/mL to about 130 mg/mL, or about 100 mg/mL to about 120 mg/mL, or about 50 mg/mL to about 100 mg/mL, or about 60 mg/mL to about 90 mg/mL, or about 90 mg/mL to about 120 mg/mL, for example, about 150 mg/mL based upon the weight of the KZR-616 maleate salt or about 125 mg/mL based upon the weight of the KZR-616 free base. In embodiments, the KZR-616 concentration is measured upon reconstitution of the lyophilized formulation after the lyophilized formulation has been stored for at least six months at, e.g., 5° C., 25° C., or 40° C.

The pharmaceutical formulations disclosed herein can comprise a sugar, e.g., a reducing or non-reducing sugar, or a sugar alcohol. Formulations of KZR-616 or salt thereof having a sugar are stable when stored at 5° C., 25° C., and 40° C. for at least 6 months. In embodiments, the sugar can comprise mannitol, trehalose, dextrose, glucose, fructose, mannose, galactose, xylose, sucrose, lactose, sorbitol, dextran, erythritol, or combinations thereof. In embodiments, the sugar can comprise mannitol and/or trehalose. In embodiments, the sugar comprises trehalose.

In embodiments, the formulations comprise the sugar component, based upon the total weight of the formulation, at an amount of, e.g., about 0.01 wt % to about 10 wt %, or about 0.1 wt % to about 10 wt %, or about 0.1 wt % to about 9 wt %, or about 0.1 wt % to about 8 wt %, or about 0.1 wt % to about 7 wt %, or about 0.1 wt % to about 6 wt %, or about 0.1 wt % to about 5 wt %, or 0.1 wt % to about 4 wt %, or about 0.5 wt % to about 5 wt %, or about 0.5 wt % to about 4 wt %, or about 0.5 wt % to about 3 wt %, or about 0.5 wt % to about 2 wt %, or about 1 wt % to about 5 wt %, or about 1 wt % to about 4 wt %, or about 1 wt % to about 3 wt %, or about 1 wt % to about 2 wt %, or about 1.5 wt % to about 5 wt %, or about 1.5 wt % to about 4 wt %, or about 1.5 wt % to about 3 wt %, or about 1.5 wt % to about 2 wt %, or about 2 wt % to about 5 wt %, or about 3 wt % to about 5 wt %, for example about 2 wt % based upon the total weight of the formulation. In embodiments, the moisture content is measured after the lyophilized formulation has been stored for at least six months at, e.g., 5° C., 25° C., or 40° C. In embodiments, the formulations described herein can have a moisture content of up to 5% by weight, such as up to 4%, 3%, 2%, 1.5%, 1%, or 0.5%. In embodiments, the formulations described herein can have a moisture content of up to 5%, up to 4%, 3%, 2%, 1.5%, 1%, or 0.5% after storage at 5° C., 25° C., or 40° C. for a given amount of time, such as, at least six months, for example, a moisture content of less than 1% after storage at 5° C., 25° C., or 40° C. for at least six months.

In some cases, the formulations described herein can optionally comprise a buffer. In some cases, the formulation does not comprise a buffer. As used herein, the term, "buffer" refers to a buffer that is in addition to any salt form of KZR-616. In embodiments, the secondary buffer can comprise succinate, citrate, phosphate, histidine, acetate, maleate, gluconate, or combinations thereof. In embodiments, the buffer comprises a succinate buffer. In embodiments, the buffer, such as a succinate buffer, can have a concentration, as measured prior to lyophilization, of about 1 mM to about 50 mM, or about 1 mM to about 40 mM, or about 1 mM to about 30 mM, or about 1 mM to about 25 mM, or about 1 mM to about 20 mM, or about 1 mM to about 15 mM, or about 1 mM to about 10 mM, or about 2 mM, or about 3 mM, or about 4 mM, or about 5 mM, or about 6 mM, or about 7 mM, or about 8 mM, or about 9 mM, or about 10 mM, or about 11 mM, or about 12 mM, or about 13 mM, or about 14 mM, or about 15 mM, for example, 10 mM.

The formulations described herein can optionally further comprise a bulking agent, in addition to the sugar or instead of the sugar. Additives contemplated, such as bulking agents, include glycine, serine, cysteine, or a combination thereof.

In aspects, the formulations described herein can have the following advantages: (1) the lyophile displays a cake that upon reconstitution is visually clear and/or free of particles; (2) the moisture content of the lyophile is less than or equal to 1% (by weight or mol); (3) the freeze-drying time and/or reconstitution time of lyophilized cake is faster compared to other pharmaceutical formulations, as detailed below in the Examples; and/or (4) the formulation has desired stability, e.g., less than 0.5% degradation (by weight or mol) as determined at 5° C. for at least 6 months, less than 7% degradation (by weight or mol) as determined at 25° C. for at least 6 months, and less than 20% degradation (by weight or mol) as determined at 40° C. for at least 6 months.

The formulations disclosed herein can have a pH, as measured prior to lyophilization, of 3.0 to 4.5, e.g., 3.8 to 4.3. In some cases, the pH, prior to lyophilization, is 4.2. In embodiments, the formulations described herein, when measured upon reconstitution, can have a pH of about 2 to about 8 or about 3 to about 5 at a temperature of about 25° C. In embodiments, the formulations, when measured upon reconstitution, can have a pH at a temperature of about 25° C., of about 3.1 to about 4.9, or about 3.2 to about 4.8, or about 3.3 to about 4.7, or about 3.4 to about 4.6, or about 3.5 to about 4.5, or about 3.6 to about 4.4, or about 3.7 to about 4.3, or about 3.7 to about 4.3, or about 3.8 to about 4.3, or about 3.9 to about 4.2, for example, about 4.2 at a temperature of about 25° C. In embodiments, the pH is measured upon reconstitution of the lyophilized formulation after the lyophilized formulation has been stored for at least six months at, e.g., 5° C., 25° C., or 40° C.

In embodiments, the formulations can have a purity of the API (KZR-616 or salt thereof) of greater than 70% after storage at 5° C., 25° C., or 40° C. for at least six months, such as greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99%, after storage at 5° C., 25° C., or 40° C. for at least six months, for example, greater than 93% after storage at 5° C., 25° C., or 40° C. for at least six months. By purity of greater than 70% is meant that the amount of API in the formulation after the indicated storage time and temperature is greater than 70% (by weight or mol) of the amount of API in the formulation prior to storage.

In embodiments, the formulations disclosed herein can have a reconstitution time of less than or equal to ten minutes, such as less than or equal to 9 minutes, less than or equal to 8 minutes, less than or equal to 7 minutes, less than or equal to 6 minutes, less than or equal to 5 minutes, less than or equal to 4.5 minutes, less than or equal to 4 minutes, less than or equal to 3.5 minutes, or less than or equal to 3 minutes. In embodiments, the formulations can have a reconstitution time of less than or equal to ten minutes after storage at 5° C., 25° C., or 40° C. for at least six months, such as less than or equal to 9 minutes, less than or equal to 8 minutes, less than or equal to 7 minutes, less than or equal to 6 minutes, less than or equal to 5.5 minutes, less than or equal to 5 minutes, less than or equal to 4 minutes, less than or equal to 3.5 minutes, less than or equal to 3 minutes, for example, the formulations herein can have a reconstitution time of less than or equal to 4.5 minutes after storage at 5° C., 25° C., or 40° C. for at least six months. As used herein, the term "reconstitution time" refers to the amount of time it takes to completely dissolve a lyophilized formulation according to the Reconstitution Method, detailed below.

Reconstituted Formulation

The formulations disclosed herein can be lyophilized to a cake form, powder form, or the cake and/or powder may be further processed into gels, foams, aerosols, films, or other formulations. In embodiments, the formulations can be reconstituted with a solvent for administration to a subject in need thereof. Thus, provided herein are kits comprising the formulation as a lyophilized composition and a reconstituting solution.

Provided herein are reconstituted formulations of KZR-616 or salt thereof comprising a lyophilized pharmaceutical formulation described herein and a solvent for reconstitution. The solvent for reconstitution can comprise any solvent or solvents suitable to one of ordinary skill in the art. In embodiments, the solvent for reconstitution can comprise water for injection ("WFI"), saline solution, or aqueous 5% dextrose. In some specific embodiments, the solvent for reconstitution comprises water for injection. In embodiments, the solvent for reconstitution does not comprise chloride ion (e.g., is not saline). In embodiments, the reconstituted formulation can be used for subcutaneous injection.

In embodiments, the osmolality of the reconstituted formulations can be from 200 mOsm to 400 mOsm, such as, from 250 mOsm to 400 mOsm, or from 275 mOsm to 350 mOsm, or from 275 mOsm to 325 mOsm, for example about 300 mOsm, a near isotonic osmolality.

In embodiments, the reconstituted formulations herein can have absorption rates, as measure by $T_{1/2}$, of at least 10% faster than that of a formulation comprising KZR-616 or salt thereof and polysorbate-80 ("PS-80") (a "PS-80 formulation"), such as at least 20% faster, at least 30% faster, at least 40% faster, at least 50% faster, or at least 60% faster, for example, at least 50% faster than that of a PS-80 formulation.

In embodiments, the reconstituted formulations described herein can have a $C_{max}$ of at least 50% that of a PS-80 formulation, such as at least 100%, at least 110%, at least 120%, at least 130%, at least 140%, at least 150%, at least 160%, at least 170%, or at least 180%, for example, at least 150% that of a PS-80 formulation.

Method of Preparing

The pharmaceutical formulations disclosed herein can be prepared by, e.g., admixing the KZR-616 or a salt thereof and the sugar to form a solution. In embodiments, the solution is an aqueous solution. In embodiments, the solution can be lyophilized to form the lyophilized pharmaceutical formulation. The method of preparing the pharmaceutical formulation can further comprise reconstituting the lyophilized formulation with a solvent to form a reconstituted formulation described herein. The solvent used to form a reconstituted formulation can be any solvent suitable to one of skill in the art to reconstitute a lyophilized formulation, for example, the solvent can comprise water or aqueous 5% dextrose.

Method of Treating

Another aspect of the disclosure provides a method of treating an immune-related disease in a subject by administering the reconstituted formulations as described herein. In some cases, the disease is psoriasis, dermatitis, systemic scleroderma, sclerosis, Crohn's disease, ulcerative colitis; respiratory distress syndrome, meningitis; encephalitis; uveitis; colitis; glomerulonephritis; eczema, asthma, chronic inflammation; atherosclerosis; leukocyte adhesion deficiency; rheumatoid arthritis; systemic lupus erythematosus (SLE); diabetes mellitus; multiple sclerosis; Reynaud's syndrome; autoimmune thyroiditis; allergic encephalomyelitis; Sjogren's syndrome; juvenile onset diabetes; tuberculosis, sarcoidosis, polymyositis, granulomatosis, vasculitis; pernicious anemia (Addison's disease); a disease involving leukocyte diapedesis; central nervous system (CNS) inflammatory disorder; multiple organ injury syndrome; hemolytic anemia; myasthenia gravis; antigen-antibody complex mediated disease; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia. In various cases, the disorder is lupus, lupus nephritis, rheumatoid arthritis, diabetes, scleroderma, ankylosing spondylitis, psoriasis, multiple sclerosis, Hashimoto's disease, meningitis, or inflammatory bowel disease. In embodiments, the disease is lupus nephritis or SLE.

Another aspect of the disclosure provides a method of treating inflammation in a subject by administering a reconstituted formulation as disclosed herein.

Reconstitution Method

A lyophilized pharmaceutical formulation, as described herein, is placed in a vial. An amount of filtered Milli-Q® ("MQ") water, such as a milliliter, is added to said vial. Upon addition of the MQ water, a timer is started to measure the amount of time for the lyophilized pharmaceutical formulation to reconstitute and/or completely dissolve. Every thirty seconds the vial with the MQ water and the lyophilized formulation is gently swirled until the reconstitution is completed.

EXAMPLES

Example 1

The stability of KZR-616 in various formulation conditions was examined in this Lyophilization Formulation Development study. The conditions investigated in this study included buffered (10 mM succinate) and unbuffered formulations with various excipients (L-Glycine, Mannitol, and Trehalose) at different pH values (3.9-4.2). The stability of KZR-616 at 150 mg/mL in different formulations was examined under static storage conditions at refrigerated (5° C.), ambient (25° C.), and accelerated (40° C.) temperatures for up to 6 months. Over the course of this 6 month study, Reversed Phase HPLC (RP-HPLC) analysis was the main analytical method used for monitoring KZR-616 stability.

Lyophilized cakes displayed consistent appearances over 6 months of storage at all storage temperatures. Some increase in yellow coloration in the lyophiles were observed over time, especially at 25° C. and 40° C. This yellow coloration was more apparent after reconstitution. Following reconstitution, all formulations were free of visible particles. Over 6 months of storage, formulation pH and KZR-616 concentration values remained comparable to values observed at time zero. Reconstitution times also remained consistent over 6 months of storage, at less than four minutes and thirty seconds.

The stability of KZR-616 was evaluated using RP-HPLC analysis. Following 6 months of storage at 5° C., all formulations displayed slight decreases in main peak percentages to those observed at time zero. Following storage at 25° C., formulations displayed decreases in main peak percentages, with unbuffered trehalose-containing formulations displaying higher main peak percentages than other formulations. Following 6 months of storage at 40° C., all formulations displayed significant decreases in main peak percentages, mostly due to increases in degradant peaks Unknown RRT=0.1, KZR-59587, Unknown RRT=0.5, KZR-0214143, and Unknown RRT=2.2. The unbuffered trehalose-containing formulations with or without mannitol displayed the highest main peak percentages among the tested formulations.

As no degradation was expected during 5° C., a lyophilization cycle optimization study was conducted to determine if it was possible to improve the stability of the formulation by further reducing the residual moisture content though lyophilization cycle optimization. This Moisture Optimization Study was performed by lyophilizing the leading formulation with various secondary shelf temperatures of 10° C., 25° C., 35° C. and 50° C. However, after 4 weeks of storage at 40° C., no differences were observed in visual appearance, pH, concentration, reconstitution times, and peak percentages by RP-HPLC, regardless of secondary drying shelf temperature.

Based on the results of this study, the leading formulation for lyophilized 150 mg/mL KZR-616 was identified as a formulation containing 2% trehalose at pH 4.2 and no additional buffer.

Materials

The active pharmaceutical ingredient (API) examined in this study was KZR-616. The material used for this study was comprised of the following:
(1) Drug Substance (DS): KZR-616 maleate salt (Lot A)
(2) Drug Substance (DS): KZR-616 maleate salt (Lot B)
(3) Reference Standard (RS):KZR-616 maleate material The Drug Substance was stored at 2-8° C. prior to use.

Formulation Parameters

In the accelerated stability study, the following parameters were held constant:
(1) Fill volume: 1.0 mL
(2) Buffer Concentration: 10 mM or 0 mM The following formulation (F1-F9) parameters were examined:
(1) API Concentrations: 150 mg/mL
(2) Buffers: Succinate
(3) pH: 3.9-4.2
(4) Tonicity modifier: 0.2% Glycine, 1% Trehalose, 0.4% Mannitol, 0.4% Glycine, 1% Mannitol, 2% Trehalose, 0.3% Glycine, 0.8% Mannitol

TABLE 1

Formulation Matrix for the Formulation Development Study

| Formulation | Buffer (10 mM) | pH | L-Glycine (%) | Mannitol (%) | Trehalose (%) | API (mg/mL) |
|---|---|---|---|---|---|---|
| F1 | N/A | 4.2 | 0.2 | 0 | 1 | 150 |
| F2 | N/A | 4.2 | 0 | 0.4 | 1 | 150 |
| F3 | N/A | 4.2 | 0.4 | 0 | 0 | 150 |
| F4 | N/A | 4.2 | 0 | 1 | 0 | 150 |
| F5 | N/A | 4.2 | 0 | 0 | 2 | 150 |
| F6 | Succinate | 4.2 | 0.3 | 0 | 0 | 150 |
| F7 | Succinate | 4.2 | 0 | 0.8 | 0 | 150 |
| F8 | Succinate | 3.9 | 0.3 | 0 | 0 | 150 |
| F9 | Succinate | 3.9 | 0 | 0.8 | 0 | 150 |

Formulation Preparations

Lyophilization Cycle Development #1

To determine the parameters for the conservative cycle, Sub-ambient differential scanning calorimetry (DSC) (PerkinElmer Pyris Diamond) was performed on three representative formulations F3, F4, and F5, containing glycine, mannitol or trehalose, respectively. The method program used is as follows: isothermal hold at −60° C. for 1 minute and heat from −60° C. to 25° C. at 5° C./minute. F3, F4, and F5 showed glass transition temperatures ($T_g$) of −16° C., −15° C., and −33° C., respectively, Table 1. Crystallization occurred for F4 with devitrification temperature ($T_d$) at −10° C., therefore an annealing step was added to obtain more complete crystallization before primary drying. This data was implemented in the initial lyophilization cycle, Table 3.

Based on the results from the sub-ambient DSC, a conservative lyophilization cycle was designed to generate samples with a residual moisture concentration <1%. Table 3 describes the parameters for the initial conservative cycle.

KZR-616 maleate was dissolved in filtered Milli-Q® (MQ) water at a target concentration of 170 mg/mL, KZR-616 in MQ was then heated to 60° C. for approximately 2 minutes to dissolve the drug substance into solution. Formulations were prepared as 10× stocks, and spiked into aliquots of the DS/MQ solution at a ratio of 1:9 (Buffer: DS). Each formulation's pH was titrated to target pH with NaOH. Under aseptic conditions in the BSC, all samples were sterile-filtered through 0.2 μm filters and filled into 3 cc vials at a 1.0 mL fill volume. The samples were partially stoppered with sterile stoppers, placed in the lyophilizer, and surrounded by empty vials. The samples were lyophilized using the parameters detailed in Table 3. Following the initial lyophilization cycle, the samples were reconstituted with 1 mL of filtered MQ water and analyzed. Lyophilization Cycle Development formulations were prepared with respect to Table 2.

TABLE 2

Formulation Matrix for the Lyophilization Cycle Development #1

| Formulation | Buffer (10 mM) | pH | L-Glycine (%) | Mannitol (%) | Trehalose (%) | API (mg/mL) |
|---|---|---|---|---|---|---|
| F1 | N/A | 4.2 | 0.5 | 0 | 1 | 150 |
| F2 | N/A | 4.2 | 0 | 1 | 1 | 150 |
| F3 | N/A | 4.2 | 0.7 | 0 | 0 | 150 |
| F4 | N/A | 4.2 | 0 | 2 | 0 | 150 |
| F5 | N/A | 4.2 | 0 | 0 | 3 | 150 |
| F6 | Succinate | 4.2 | 0.6 | 0 | 0 | 150 |
| F7 | Succinate | 4.2 | 0 | 1 | 0 | 150 |
| F8 | Succinate | 3.9 | 0.6 | 0 | 0 | 150 |
| F9 | Succinate | 3.9 | 0 | 1 | 0 | 150 |

TABLE 3

Example of Parameters for the Initial Conservative Cycle

| Step | Temperature | Time | Ramp Rate (° C./min) | Chamber Pressure |
|---|---|---|---|---|
| Loading | 5° C. | 10 minutes | N/A | N/A |
| Freezing | 5° C. to −50° C. | 55 minutes | 1° C./min | N/A |
|  | −50° C. | 120 minutes | N/A | N/A |
| Annealing | −50° C. to −10° C. | 40 minutes | 1° C./min | N/A |
|  | −10° C. | 120 minutes | N/A | N/A |
|  | −10° C. to −20° C. | 10 min | 1° C./min | N/A |
|  | −20° C. | 60 min | N/A | N/A |
| Primary Drying | −20° C. | N/A* | N/A* | 100 mTorr |
| Secondary Drying | −20° C. to 25° C. | 45 minutes | 1° C./min | 100 mTorr |
|  | 25° C. | 480 minutes | N/A | 100 mTorr |

Lyophilization Cycle Development #2

KZR-616 was dissolved in filtered MQ water at a target concentration of 170 mg/mL. KZR-616 in MQ was then heated to 60° C. for approximately 2 minutes to dissolve the drug substance into solution. Formulations were prepared as 10× stocks and spiked into aliquots of the DS/MQ solution at a ratio of 1:9 (Buffer: DS). Each formulation's pH was titrated to target pH with NaOH. Under aseptic conditions in the BSC, all samples were sterile-filtered through 0.2 μm filters and filled into 3 cc vials at a 1.0 mL fill volume. The formulation matrix (buffer, bulking agent concentrations, pH) are outlined in Table 1. The samples were partially stoppered with sterile stoppers, placed in the freeze dryer and surrounded by empty vials. The samples were lyophilized using the parameters detailed in Table 4. Following lyophilization, the samples were reconstituted with 1 mL of filtered MQ water and analyzed following the methods outlined in Table 8.

TABLE 4

Example of Parameters for the Second Lyophilization Cycle

| Step | Temperature | Time | Ramp Rate (° C./min) | Chamber Pressure |
|---|---|---|---|---|
| Loading | 5° C. | 10 minutes | N/A | N/A |
| Freezing | 5° C. to −50° C. | 55 minutes | 1° C./min | N/A |
|  | −50° C. | 120 minutes | N/A | N/A |
| Annealing | −50° C. to −10° C. | 40 minutes | 1° C./min | N/A |
|  | −10° C. | 120 minutes | N/A | N/A |
| Primary Drying | −10° C. | 600 minutes | N/A | 70 mTorr |
| Secondary Drying | −10° C. to 25° C. | 35 minutes | 1° C./min | 70 mTorr |
|  | 25° C. | 480 min | N/A | 70 mTorr |

Accelerated Stability Study

Once IBI identified a lyophilization cycle that produced elegant cakes with a moisture content value less than 1%, the cycle was repeated to confirm the cycle results and prepare samples for the Accelerated Stability Study.

KZR-616 was dissolved in filtered MQ water as a stock solution at a concentration of 170 mg/mL. KZR-616 stock solution was heated to 60° C. for approximately 2 minutes to completely dissolve the drug substance. Formulation buffers were prepared as 10× stock solutions. Each formulation was prepared with 10× buffer stock solution, DS stock (170 mg/mL), and MQ to target the final concentration of 150 mg/mL. The pH of each formulation was adjusted to the target pH using NaOH. Under aseptic conditions in the BSC, all samples were sterile-filtered through 0.2 μm filters and filled into 3 cc vials at a 1.0 mL fill volume. The samples were partially stoppered with sterile stoppers, placed in the freeze dryer and surrounded by empty vials. The samples were lyophilized using the parameters detailed in Table 4.

Following lyophilization, the product quality and integrity was evaluated by comparing the Pre-lyophilization liquid samples, lyophilized cakes and reconstituted samples using the analytical methods listed in Table 9.

Moisture Optimization

Two different drug substance lots (KZR-0214142 and C15072369-FF1600) of KZR-616 were individually dissolved in MQ to a concentration of 170 mg/mL and were heated to 60° C. for approximately 2 minutes to completely dissolve the drug substance. Both 170 mg/ml preparations were then diluted with 10× target buffer (F5, 2% trehalose at pH 4.2) to 150 mg/ml. The pH of each formulation was titrated to the target pH using NaOH. Under aseptic conditions in the BSC, all samples were sterile-filtered through 0.2 μm filters and filled into 3 cc vials at a 1.0 mL fill volume. The samples were partially stoppered with sterile stoppers, placed in the freeze dryer, and surrounded by empty vials to prevent movement. The samples were lyophilized using the parameters detailed in Table 5.

The lyophilization cycle was pre-programmed through the first secondary drying temperature (10° C.). Following the first secondary drying temperature, all following operations of the lyophilizer were performed manually to accommodate all shelf temperatures. Each of the secondary drying temperatures was performed for a minimum of at least 8 hours. At the end of each secondary drying temperature the vials for that temperature were stoppered, the lyophilizer was manually stopped, and the vacuum was purged. Afterwards, the stoppered tray was removed and the lyophilizer was manually restarted for the next secondary drying temperature. The last step was repeated for each secondary drying temperature. Following lyophilization, samples were put into stability storage conditions and T=0 samples were reconstituted with 1 mL of filtered MQ water and analyzed. Methods of analyses are outlined in Table 8.

TABLE 5

Example of Parameters for the Optimized Lyophilization Cycle

| Step | Temperature | Time (min) | Ramp Rate (° C./min) | Chamber Pressure (mT) |
|---|---|---|---|---|
| Loading | 5° C. | 10 min | N/A | N/A |
| Freezing with Annealing | 5° C. to −50° C | 55 min | 1.0° C./min | N/A |
|  | −50° C. | 120 min | N/A | N/A |
|  | −50° C. to −10° C. | 40 min | 1.0° C./min | N/A |
|  | −10° C. | 120 min | N/A | N/A |
| Primary Drying | −10° C. | 600 min* | N/A | 70 mT |
| Secondary Drying | −10° C. to 10° C. | 20 min | 1.0° C./min | 70 mT |
|  | 10° C. | 960 min | N/A | 70 mT |
|  | 25° C.‡ | 480 min | N/A | 70 mT |
|  | 35° C.‡ | 960 min | N/A | 70 mT |
|  | 50° C.‡ | 480 min | N/A | 70 mT |

Stress Conditions
Accelerated Stability

The stability of the lyophilized formulations was studied under the following conditions described in Table 6.

TABLE 6

Storage Conditions for Accelerated Stability Study

| Storage Conditions | Time Points |
|---|---|
| 2-8° C. (lyophilized) | 1, 2, 3, and 6 months |
| 25° C. (reconstituted liquid) | 0, 8, 24 hours |
| 25° C. (lyophilized) | 1, 2, 3, and 6 months |
| 40° C. (lyophilized) | 1, 2, 3, and 6 months |

Moisture Optimization

The stability of the lyophilized formulations was studied under the following conditions described in Table 7.

TABLE 7

Storage Conditions for Moisture Optimization Study

| Storage Conditions | Time Points |
|---|---|
| 40° C. (lyophilized) Lot A | 0, 1, 2, 4 week |
| 40° C. (lyophilized) Lot B | 0 and 4 week |

Analytical Methods
Lyophilization Cycle Development (1 & 2)

A variety of analyses were performed for the samples following lyophilization cycles 1 and 2. Table 8 summarizes these analyses for the stability study.

TABLE 8

Analytical methods - Lyophilization Cycle Development

| Analytical Method | Purpose |
| --- | --- |
| Visual inspection | Clarity, color, and visible particles |
| Osmolality | Osmolality |
| pH | pH |
| Reconstitution time | Measure rate of reconstitution |
| Sub-ambient DSC | Identifying temperature-dependent transition phases |
| Karl Fischer Titration | Measure moisture content |
| RP-HPLC | Chemical modification (hydrophobicity) |
| FT-IR | Infrared spectrum- Structural integrity |

Accelerate Stability Study

A variety of analyses were performed for the lyophilized samples following incubation at each temperature and time point. At each time below, samples were analyzed for visual appearance, pH, concentration, reconstitution time, RP-HPLC, and moisture content. Table 9 summarizes the various analyses for the Accelerated Stability Study.

TABLE 9

Analytical Methods - Accelerated Stability Study

| Analytical Method | Purpose |
| --- | --- |
| Visual inspection | Clarity, color, and visible particles |
| Osmolality | Osmolality |
| pH | pH |
| Spectrophotometry | Concentration analysis |
| Reconstitution time | Measure rate of reconstitution |
| Karl Fischer Titration | Measure moisture content |
| RP-HPLC | Chemical modifications (hydrophobicity) |

TABLE 10

Time Point Analytical Methods—Accelerated Stability Study

| Analytical Methods | T = 0 | 8 hrs | 24 hrs days | 1 month | 2 months | 3 months | 6 months |
| --- | --- | --- | --- | --- | --- | --- | --- |
| Visual Appearance | X | X | X | X | X | X | X |
| pH | X | X | X | X | X | X | X |
| Spectrophotometry | X | X | X | X | X | X | X |
| Osmolality | X |  |  |  |  | X | X |
| Reconstitution Time | X |  |  | X | X | X | X |
| Karl Fischer | X |  |  | X | X | X | X |
| RP-HPLC | X | X | X | X | X | X | X |

The analytical methods for all the previously described studies are detailed below.

(1) Visual Inspection: Visual inspection was performed under a white light source (13 W fluorescent tube) against black and white backgrounds. Digital photographs were taken for Pre-lyophilization, post-lyophilization, and reconstituted formulations.

(2) Osmolality: Osmolality was measured at time zero of each objective study.

(3) pH: pH analysis was performed with a SympHony® pH Meter (VWR Scientific, catalog #SB70P), calibrated with three pH standard solutions (pH 4, 7, and 10) with a calibration slope of 95% or higher. Samples were allowed to equilibrate to ambient temperature before measurement.

(4) Absorbance Spectrophotometry: The concentration of KZR-616 was determined via Beckman Coulter Spectrophotometer. An extinction coefficient of 1.8495 (mg/mL)-1 cm-1 was determined by generating a standard curve (1 mg/mL, 0.75 mg/mL, 0.5 mg/mL, and 0.25 mg/mL, serially diluted in MQ). KZR-616 was analyzed via a full wavelength scan and showed maximal absorbance at 272 nm. This wavelength was used to measure concentration.

(5) FTIR: Pre-lyophilization and post-lyophilization formulations were analyzed to determine the fingerprint of formulation containing bulking agents. (Performed post-lyophilization development cycle #1 and #2)

(6) Reconstitution time: Lyophilized formulations are reconstituted with one milliliter of filter water. Upon addition of water, a timer was started to measure the amount of time for KZR-616 drug formulation to reconstitute. Every thirty seconds the reconstituted vial was gently swirled. This procedure was repeated until the reconstitution was complete.

(7) Karl Fischer Titration: Post-lyophilization formulations were analyzed to determine moisture content of the lyophilized product.

(8) DSC: Sub-ambient DSC analysis was performed from −60° C. to 25° C. at 5° C./min on each formulation to determine recrystallization of bulking agents, Tg, and other significant thermal transition data in frozen state.

(9) RP-HPLC:

The RP-HPLC method used for this study was transferred from Kezar and the parameters are listed below:

Mobile Phase A: 75% 5 mM Ammonium Acetate, 25% Acetonitrile

Mobile Phase B: 65% 5 mM Ammonium Acetate, 35% Acetonitrile

Mobile Phase C: 15% 5 mM Ammonium Acetate, 85% Acetonitrile

Column: Agilent Poroshell 120 EC-C18, 4.6×75 mm, 2.7 µm (P/N: 697975-902)

Instrument: Agilent 1100 HPLC

Column temperature: 40° C.

Autosampler Temp: 5° C.

Flow rate: 1.5 mL/min

Time: 38 minutes

Detection: 210 nm

Sample Preparation: diluted to 1.8 mg/mL with 70% ACN

Load: 18 µg (10 µL at 1.8 mg/mL)

Moisture Optimization Study

A variety of analyses were performed for lyophilized samples following incubation at each temperature and time point. At each time below, samples were analyzed for visual appearance, pH, concentration, reconstitution time, RP-HPLC, and moisture content. Table 11 summarizes these analyses for the stability study.

TABLE 11

Analytical Methods for the Moisture Optimization

| Analytical Method | Purpose |
|---|---|
| Visual inspection | Clarity, color, and visible particles |
| pH | pH |
| Spectrophotometry | Concentration analysis |
| Reconstitution time | Measure rate of reconstitution |
| Karl Fischer Titration | Measure moisture content |
| RP-HPLC | Chemical modifications (hydrophobicity) |

Results and Discussion

Lyophilization Cycle Development Study

Multiple lyophilization cycles were performed to develop a lyophilization cycle that produces cakes with the following attributes:

Elegant cake

Moisture content within specification (<1.0%)

Reduction of freeze-drying time and reconstitution time of lyophilized cakes

Good product stability

FT-IR (Fourier-transform infrared spectroscopy) was performed before and after lyophilization development cycles #1 and #2. FT-IR displayed good structural stability Pre-lyophilization, lyophilized and reconstituted. The stress (pressure and temperature) attributed from lyophilization did not disrupt the structural integrity KZR-616 in various formulations.

Visual Analysis

At time zero, both development cycles displayed elegant cakes. Development cycle #1 and #2 displayed samples that were visually clear, free of particles, and slightly yellow in coloration.

Formulation Osmolality

The osmolality of the nine (9) formulations was measured following sample preparation, prior to any stress exposure. Lyophilization cycle #1 formulations and specific reagents are outlined in Table 2. After confirming the osmolality of cycle #1 formulations (Table 12), the bulking agent concentrations were decreased for cycle #2, to target isotonic osmolality's (~300 Osmo). Lyophilization cycle #2 displayed isotonic osmolality measurements Pre-lyophilization and post reconstitution (Table 12).

TABLE 12

Osmolality (Lyophilization Cycle #1 & #2)

| | Osmolality (mOsm/kg) | | | |
|---|---|---|---|---|
| | Cycle #1 | | Cycle #2 | |
| Formulation No. | Pre-lyophilization | Reconstituted | Pre-lyophilization | Reconstituted |
| F1 | 461 | 342 | 321 | 296 |
| F2 | 372 | 343 | 313 | 296 |
| F3 | 356 | 328 | 311 | 288 |
| F4 | 388 | 333 | 316 | 293 |
| F5 | 395 | 342 | 322 | 300 |
| F6 | 398 | 332 | 308 | 290 |
| F7 | 416 | 330 | 321 | 300 |
| F8 | 359 | 318 | 295 | 277 |
| F9 | 374 | 325 | 307 | 289 | pH Measurements

Lyophilization Cycles 1 and 2 displayed comparable pH values Pre-lyophilization and after reconstitution (Table 13). However, after reconstitution Lyophilization Cycle #2 displayed pH values closer to target.

TABLE 13 pH (Lyophilization Cycle #1 & #2)

| | pH | | | |
|---|---|---|---|---|
| | Cycle #1 | | Cycle #2 | |
| Sample Code | Pre-lyophilization | Reconstituted | Pre-lyophilization | Reconstituted |
| F1 | 4.15 | 4.11 | 4.21 | 4.23 |
| F2 | 4.18 | 4.14 | 4.15 | 4.16 |
| F3 | 4.15 | 4.13 | 4.23 | 4.22 |
| F4 | 4.13 | 4.13 | 4.24 | 4.22 |
| F5 | 4.08 | 4.10 | 4.20 | 4.19 |
| F6 | 4.18 | 4.18 | 4.23 | 4.18 |
| F7 | 4.07 | 4.15 | 4.28 | 4.25 |
| F8 | 3.90 | 3.90 | 3.91 | 3.87 |
| F9 | 3.81 | 3.80 | 3.95 | 3.91 |

Reconstitution Time Measurements

Following lyophilization cycles 1 and 2, formulations were reconstituted with one milliliter of filtered MQ. Upon the addition of MQ, a timer was started to measure the amount of time each formulation required to homogenize. Lyophilization cycle #1 displayed reconstitution times of 4:31 minutes or less, while cycle #2 displayed reconstitution times of 4:12 minutes or less (Table 14).

TABLE 14

Reconstitution Time (Lyophilization Cycle #1 & #2)

| Formulation | Reconstitution Time (min) | |
|---|---|---|
| No. | Cycle #1 | Cycle #2 |
| F1 | 2:50 | 3:44 |
| F2 | 1:50 | 1:54 |
| F3 | 1:35 | 2:11 |
| F4 | 1:37 | 2:24 |
| F5 | 4:31 | 2:09 |
| F6 | 4:22 | 2:49 |
| F7 | 3:12 | 2:10 |
| F8 | 1:04 | 4:12 |
| F9 | 1:15 | 2:05 |

Moisture Content Measurements (Karl Fischer)

Following lyophilization cycles 1 and 2, formulations displayed comparable moisture content values to each other (Table 15). All lyophilized formulations displayed moisture content values less than 1%. Lyophilization cycle #1 displayed moisture content values 0.28% to 0.60%. Lyophilization cycle #2 displayed moisture content values 0.21% to 0.39%.

TABLE 15

Lyophilization Cycle Moisture Content Measurements (Time Zero)

| Sample | % Moisture Content | |
|---|---|---|
| No. | Cycle #1 | Cycle #2 |
| 1% Water Std | 0.95 | |
| F1 Lyo | 0.60 | 0.39 |
| F2 Lyo | 0.54 | 0.31 |
| F3 Lyo | 0.41 | 0.27 |
| F4 Lyo | 0.30 | 0.33 |
| F5 Lyo | 0.46 | 0.30 |
| F6 Lyo | 0.28 | 0.29 |
| F7 Lyo | 0.29 | 0.21 |
| F8 Lyo | 0.43 | 0.27 |
| F9 Lyo | 0.58 | 0.28 |

RP-HPLC Analysis

Following four (4) weeks of incubation at 40° C., all reconstituted formulations showed decreases in main peak percentages (90.3%-91.7%) compared to those observed at time zero (97.7%-98.6%). RP-HPLC identified the main degradant species in the KZR-616 molecule. Peaks RRT=0.1, KZR-59587, KZR-0214143 and RRT=2.2 displayed the highest increase in peak percentages when stressed. The variation in secondary drying temperatures displayed a slight difference in main peak stability at time zero. Following four weeks at 40° C., all formulated samples displayed comparable stability (Tables 16-19).

TABLE 16

RP-HPLC (Pre-lyophilization) Integration Table (Cycle #1)

| KZR-616 | KZR-59587 (%) | Unknown RRT = 0.5 (%) | KZR-0214138 (%) | KZR-0214142 (%) | KZR-616 (%) | KZR-0214117 (%) | KZR-0214143 (%) | Total Area (mAU) |
|---|---|---|---|---|---|---|---|---|
| Ref. Std. (Beg.) | 0.4 | 0.1 | 0.0 | 0.0 | 99.3 | 0.1 | 0.1 | 15091 |
| F1 Pre-lyophilization | 0.5 | 0.1 | 0.0 | 0.1 | 99.2 | 0.1 | 0.1 | 13980 |
| F2 Pre-lyophilization | 0.6 | 0.1 | 0.0 | 0.1 | 99.0 | 0.1 | 0.1 | 13438 |
| F3 Pre-lyophilization | 0.6 | 0.1 | 0.0 | 0.0 | 99.1 | 0.1 | 0.1 | 13222 |
| F4 Pre-lyophilization | 0.6 | 0.1 | 0.0 | 0.1 | 99.1 | 0.1 | 0.1 | 13206 |
| F5 Pre-lyophilization | 0.6 | 0.1 | 0.0 | 0.0 | 99.1 | 0.1 | 0.1 | 13159 |
| F6 Pre-lyophilization | 0.6 | 0.1 | 0.0 | 0.1 | 99.1 | 0.1 | 0.1 | 12937 |
| F7 Pre-lyophilization | 0.6 | 0.1 | 0.0 | 0.1 | 99.1 | 0.1 | 0.1 | 13582 |
| F8 Pre-lyophilization | 0.7 | 0.1 | 0.0 | 0.1 | 99.0 | 0.1 | 0.1 | 12490 |
| F9 Pre-lyophilization | 0.6 | 0.0 | 0.0 | 0.0 | 99.1 | 0.1 | 0.1 | 13086 |
| Ref. Std. (End) | 0.4 | 0.1 | 0.0 | 0.0 | 99.3 | 0.1 | 0.1 | 15258 |

TABLE 17

RP-HPLC (Reconstitution) Integration Table (Cycle #1)

| KZR-616 | KZR-59587 (%) | Unknown RRT = 0.5 (%) | KZR-0214138 (%) | KZR-0214142 (%) | KZR-616 (%) | KZR-0214117 (%) | KZR-0214143 (%) | Total Area (mAU) |
|---|---|---|---|---|---|---|---|---|
| Ref. Std. (Beg.) | 0.4 | 0.1 | 0.0 | 0.0 | 99.3 | 0.1 | 0.1 | 15091 |
| F1 Reconstitution | 0.6 | 0.1 | 0.0 | 0.1 | 98.9 | 0.1 | 0.1 | 12531 |
| F2 Reconstitution | 0.5 | 0.2 | 0.0 | 0.1 | 99.1 | 0.1 | 0.1 | 13307 |
| F3 Reconstitution | 0.6 | 0.1 | 0.0 | 0.1 | 99.0 | 0.1 | 0.1 | 12689 |
| F4 Reconstitution | 0.7 | 0.1 | 0.0 | 0.1 | 99.0 | 0.1 | 0.1 | 13267 |
| F5 Reconstitution | 0.7 | 0.2 | 0.0 | 0.1 | 98.9 | 0.1 | 0.1 | 12898 |
| F6 Reconstitution | 0.6 | 0.1 | 0.0 | 0.1 | 99.0 | 0.1 | 0.1 | 12659 |
| F7 Reconstitution | 0.7 | 0.1 | 0.0 | 0.1 | 99.0 | 0.1 | 0.1 | 13176 |
| F8 Reconstitution | 0.7 | 0.0 | 0.0 | 0.1 | 99.0 | 0.1 | 0.1 | 12464 |
| F9 Reconstitution | 0.7 | 0.1 | 0.0 | 0.1 | 98.9 | 0.1 | 0.1 | 12085 |
| Ref. Std. (End) | 0.4 | 0.1 | 0.0 | 0.0 | 99.3 | 0.1 | 0.1 | 15258 |

TABLE 18

RP-HPLC (Pre-lyophilization) Integration Table (Cycle #2)

| KZR-616 | KZR-59587 (%) | Unknown RRT = 0.5 (%) | KZR-0214138 (%) | KZR-0214142 (%) | KZR-616 (%) | KZR-0214117 (%) | KZR-0214143 (%) | Total Area (mAU) |
|---|---|---|---|---|---|---|---|---|
| Ref. Std. (Beg.) | 0.8 | 0.1 | 0.0 | 0.0 | 98.9 | 0.2 | 0.1 | 14726 |
| F1 Pre-lyophilization | 1.0 | 0.0 | 0.1 | 0.1 | 98.6 | 0.1 | 0.1 | 13659 |
| F2 Pre-lyophilization | 1.0 | 0.0 | 0.1 | 0.1 | 98.7 | 0.1 | 0.1 | 15074 |
| F3 Pre-lyophilization | 1.1 | 0.0 | 0.0 | 0.1 | 98.5 | 0.1 | 0.1 | 12410 |
| F4 Pre-lyophilization | 1.1 | 0.1 | 0.1 | 0.1 | 98.5 | 0.1 | 0.1 | 13159 |
| F5 Pre-lyophilization | 1.2 | 0.1 | 0.1 | 0.1 | 98.5 | 0.1 | 0.1 | 11231 |
| F6 Pre-lyophilization | 1.1 | 0.0 | 0.0 | 0.1 | 98.5 | 0.1 | 0.1 | 12221 |
| F7 Pre-lyophilization | 1.1 | 0.0 | 0.1 | 0.1 | 98.5 | 0.1 | 0.1 | 11778 |
| F8 Pre-lyophilization | 1.1 | 0.0 | 0.0 | 0.1 | 98.5 | 0.1 | 0.1 | 13334 |
| F9 Pre-lyophilization | 1.2 | 0.0 | 0.0 | 0.1 | 98.4 | 0.1 | 0.1 | 12802 |
| Ref. Std. (End) | 0.7 | 0.1 | 0.1 | 0.0 | 99.0 | 0.1 | 0.1 | 14742 |

TABLE 19

RP-HPLC (Reconstitution) Integration Table (Cycle #2)

| KZR-616 | KZR-59587 (%) | Unknown RRT = 0.5 (%) | KZR-0214138 (%) | KZR-0214142 (%) | KZR-616 (%) | KZR-0214117 (%) | KZR-0214143 (%) | Total Area (mAU) |
|---|---|---|---|---|---|---|---|---|
| Ref. Std. (Beg.) | 0.7 | 0.1 | 0.0 | 0.0 | 98.9 | 0.1 | 0.1 | 14697 |
| F1 Reconstitution | 1.0 | 0.1 | 0.1 | 0.1 | 98.5 | 0.2 | 0.1 | 11742 |
| F2 Reconstitution | 0.9 | 0.2 | 0.0 | 0.1 | 98.6 | 0.1 | 0.1 | 13320 |

TABLE 19-continued

RP-HPLC (Reconstitution) Integration Table (Cycle #2)

| KZR-616 | KZR-59587 (%) | Unknown RRT = 0.5 (%) | KZR-0214138 (%) | KZR-0214142 (%) | KZR-616 (%) | KZR-0214117 (%) | KZR-0214143 (%) | Total Area (mAU) |
|---|---|---|---|---|---|---|---|---|
| F3 Reconstitution | 0.9 | 0.1 | 0.0 | 0.1 | 98.7 | 0.1 | 0.1 | 12860 |
| F4 Reconstitution | 1.0 | 0.1 | 0.1 | 0.1 | 98.6 | 0.1 | 0.1 | 11693 |
| F5 Reconstitution | 1.3 | 0.0 | 0.0 | 0.1 | 98.3 | 0.1 | 0.1 | 11938 |
| F6 Reconstitution | 1.3 | 0.0 | 0.0 | 0.1 | 98.3 | 0.1 | 0.1 | 11472 |
| F7 Reconstitution | 1.3 | 0.0 | 0.1 | 0.1 | 98.3 | 0.1 | 0.1 | 11066 |
| F8 Reconstitution | 0.9 | 0.0 | 0.0 | 0.1 | 98.7 | 0.1 | 0.1 | 11721 |
| F9 Reconstitution | 1.2 | 0.0 | 0.1 | 0.1 | 98.4 | 0.2 | 0.1 | 11734 |
| Ref. Std. (End) | 0.7 | 0.1 | 0.0 | 0.0 | 98.9 | 0.1 | 0.1 | 14703 |

Accelerated Stability Study

In the accelerated stability study the nine (9) buffered (Succinate) and unbuffered formulations containing various concentrations of bulking agents at pH 3.9 and pH 4.2 were prepared at 150 mg/mL.

Visual Analysis

Following 6 months of temperature related stress, the visual appearance of the lyophilized formulations displayed elegant cakes. The lyophilized cakes displayed a slight yellowish tint, which increased in color with elevated temperatures. Post reconstitution, formulations were clear, free of particles, but also displayed a yellowish coloration. Following 6 months of incubation, formulations at 5° C. and 25° C., displayed comparable coloration to time zero. At 40° C., formulations displayed a darker yellowish tint compared to time zero.

Formulation Osmolality

The osmolality of the nine (9) formulations was measured following sample preparation, prior to any stress exposure, shown on Table 20. Bulking agent concentrations were based on lyophilization cycle development #2 results, to target isotonic formulation at ~300 mOsm. Following 6 months, formulation F5 displayed comparable osmolality values to those observed at time zero.

TABLE 20

Osmolality (Time Zero & F5 T = 6 Month)

| Formulation No. | Osmolality (mOsm/kg) | |
|---|---|---|
| | Pre-lyophilization | Reconstituted |
| F1 | 316 | 298 |
| F2 | 314 | 293 |
| F3 | 309 | 292 |
| F4 | 315 | 296 |
| F5 | 324 | 305 |
| F6 | 314 | 304 |
| F7 | 325 | 306 |
| F8 | 295 | 281 |
| F9 | 308 | 290 |
| F5 T = 6 Month 5° C. | — | 305 |
| F5 T = 6 Month 25° C. | — | 306 |
| F5 T = 6 Month 40° C. | — | 308 | pH Measurements

The pHs of the nine (9) formulations were measured at every time point following temperature related stresses. Following 6 months, formulations displayed comparable pH values to time zero, shown on Table 21.

TABLE 21 pH (Time Zero & 6 Month)

| | pH | | | | |
|---|---|---|---|---|---|
| | T = 0 | | T = 6 Month | | |
| Formulation No. | Pre-lyophilization | Recon. | 5° C. | 25° C. | 40° C. |
| F1 | 4.05 | 4.09 | 4.14 | 4.18 | 4.25 |
| F2 | 4.15 | 4.17 | 4.22 | 4.28 | 4.36 |
| F3 | 4.15 | 4.16 | 4.22 | 4.24 | 4.31 |
| F4 | 4.08 | 4.09 | 4.13 | 4.21 | 4.29 |
| F5 | 4.11 | 4.14 | 4.15 | 4.29 | 4.31 |
| F6 | 4.15 | 4.19 | 4.20 | 4.23 | 4.29 |
| F7 | 4.21 | 4.27 | 4.31 | 4.31 | 4.41 |
| F8 | 3.82 | 3.85 | 3.88 | 3.92 | 4.05 |
| F9 | 3.90 | 3.93 | 3.95 | 3.99 | 4.15 |

Concentration Measurements

Following 6 months, formulations displayed comparable concentration measurements to those observed at time zero (Table 22).

TABLE 22

Concentration (Time Zero & 6 Month)

| | Concentration (mg/mL) | | | | |
|---|---|---|---|---|---|
| | T = 0 | | T = 6 Month | | |
| Formulation No. | Pre-lyophilization | Recon. | 5° C. | 25° C. | 40° C. |
| F1 | 150.2 | 137.9 | 139.4 | 141.9 | 151.7 |
| F2 | 151.8 | 134.0 | 140.2 | 142.3 | 148.6 |
| F3 | 151.3 | 137.4 | 140.5 | 142.2 | 152.2 |
| F4 | 153.2 | 137.4 | 139.3 | 143.2 | 151.8 |
| F5 | 151.4 | 136.3 | 139.2 | 143.1 | 148.3 |
| F6 | 150.7 | 141.7 | 140.2 | 143.2 | 154.7 |
| F7 | 148.9 | 134.5 | 139.6 | 134.6 | 152.2 |
| F8 | 147.8 | 135.4 | 140.3 | 142.9 | 158.3 |
| F9 | 147.5 | 132.1 | 140.1 | 134.9 | 151.2 |

Reconstitution Time Measurements

At each time point following lyophilization, formulations were reconstituted with one milliliter of filtered MQ. Upon the addition of MQ, a timer began to measure the amount of time each formulation required to homogenize. Following 6 months, formulations displayed comparable reconstitution times to time zero. After 6 months, all formulations displayed reconstitution times less than three minutes and thirty seconds (Table 23).

TABLE 23

| | Reconstitution Time (Time Zero & 6 Month) | | | |
|---|---|---|---|---|
| | | Reconstitution Time (min) | | |
| Sample No. | T = 0 | 5° C. | 25° C. | 40° C. |
| F1 | 2:43 | 1:40 | 1:53 | 1:38 |
| F2 | 1:38 | 2:17 | 2:16 | 1:27 |
| F3 | 4:12 | 1:50 | 1:57 | 1:31 |
| F4 | 2:15 | 3:21 | 2:12 | 1:38 |
| F5 | 2:09 | 2:22 | 2:27 | 1:58 |
| F6 | 2:19 | 1:57 | 2:06 | 1:40 |
| F7 | 2:00 | 2:15 | 1:50 | 1:18 |
| F8 | 2:05 | 2:48 | 1:58 | 1:23 |
| F9 | 2:21 | 2:00 | 2:19 | 1:30 |

Moisture Content Measurement (Karl Fischer)

Following 6 months of incubation, formulations displayed comparable moisture content values to time zero (Table 24). All lyophilized formulations showed continued to display moisture content values less than 1%.

TABLE 24

| | Moisture Content (Time Zero & 6 Month) | | | |
|---|---|---|---|---|
| | | % Moisture Content | | |
| Sample No. | T = 0 | 5° C. | 25° C. | 40° C. |
| 1% Water Std | | 1.02 | | |
| F1 Lyo | 0.91 | 0.27 | 0.25 | 0.24 |
| F2 Lyo | 0.38 | 0.27 | 0.25 | 0.30 |
| F3 Lyo | 0.24 | 0.19 | 0.35 | 0.26 |
| F4 Lyo | 0.28 | 0.21 | 0.22 | 0.27 |
| F5 Lyo | 0.22 | 0.26 | 0.31 | 0.31 |
| F6 Lyo | 0.37 | 0.29 | 0.65 | 0.30 |
| F7 Lyo | 0.24 | 0.28 | 0.39 | 0.19 |

TABLE 24-continued

| | Moisture Content (Time Zero & 6 Month) | | | |
|---|---|---|---|---|
| | | % Moisture Content | | |
| Sample No. | T = 0 | 5° C. | 25° C. | 40° C. |
| F8 Lyo | 0.32 | 0.26 | 0.29 | 0.30 |
| F9 Lyo | 0.30 | 0.20 | 0.19 | 0.22 |

RP-HPLC Analysis

Figure 1A:
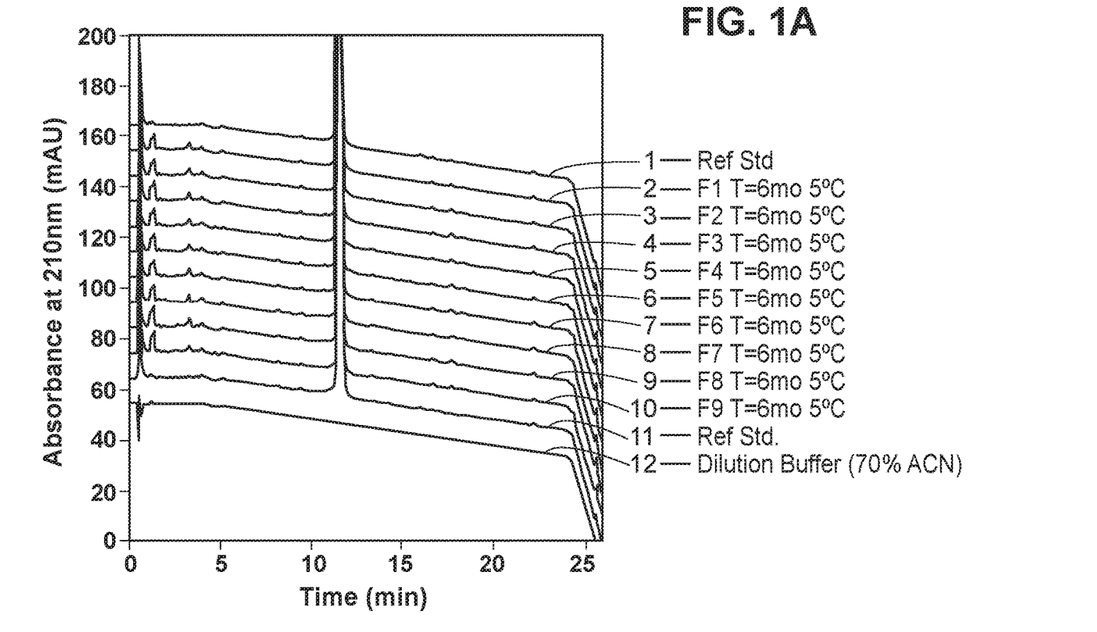
FIG. 1A shows RP-HPLC analysis for various formulations after storage for 6 months at 5° C.
Figure 1B:
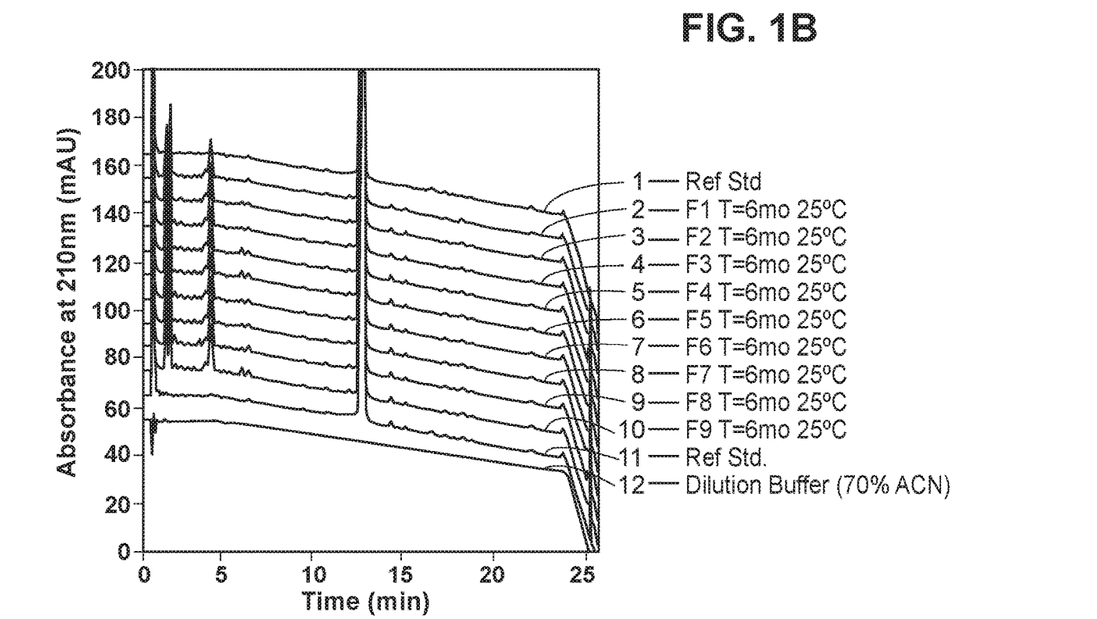
FIG. 1B shows RP-HPLC analysis for various formulations after storage for 6 months at 25° C.
Figure 1C:
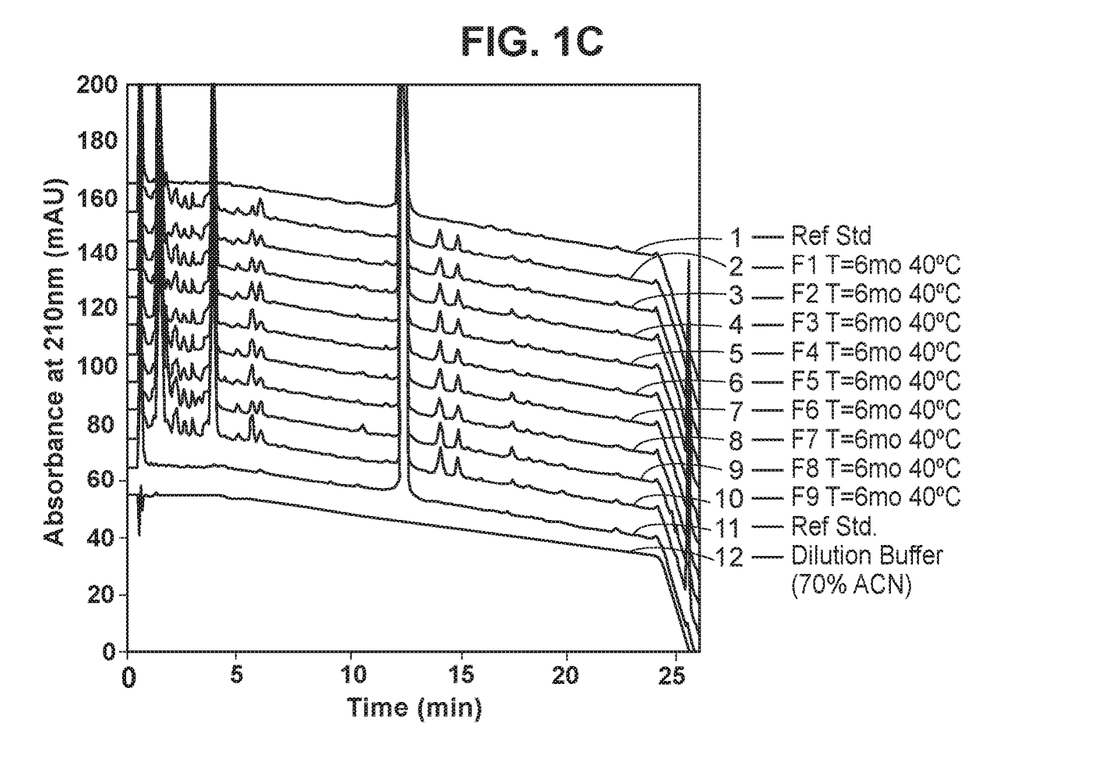
FIG. 1O shows RP-HPLC analysis for various formulations after storage for 6 months at 40° C.
Figure 2A:
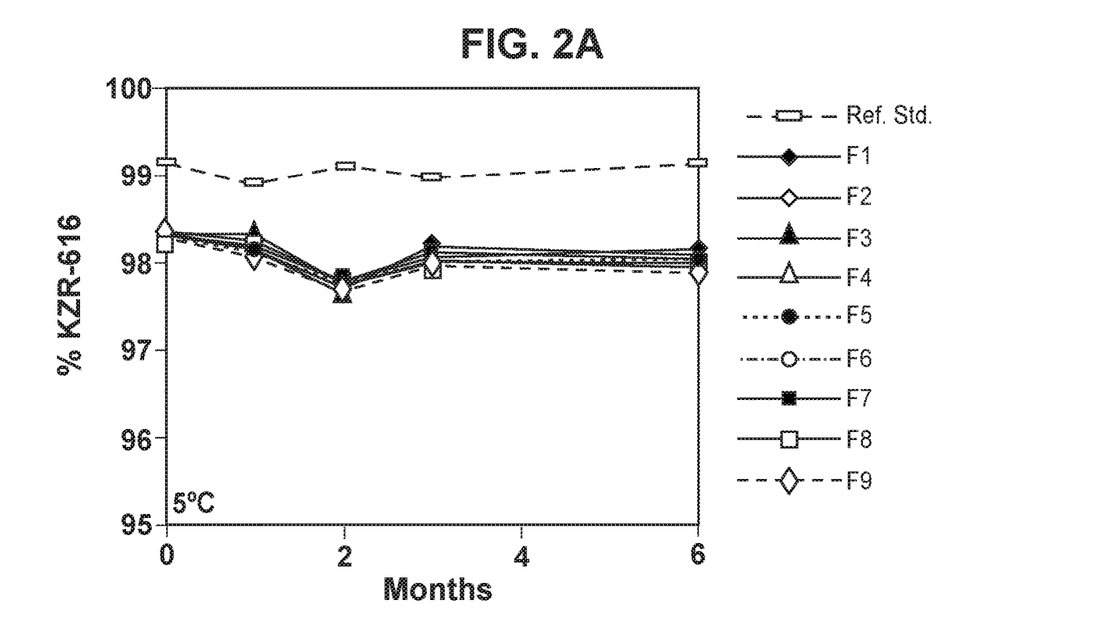
FIG. 2A shows RP-HPLC analysis trends for various formulations after storage for 6 months at 5° C.
Figure 2B:
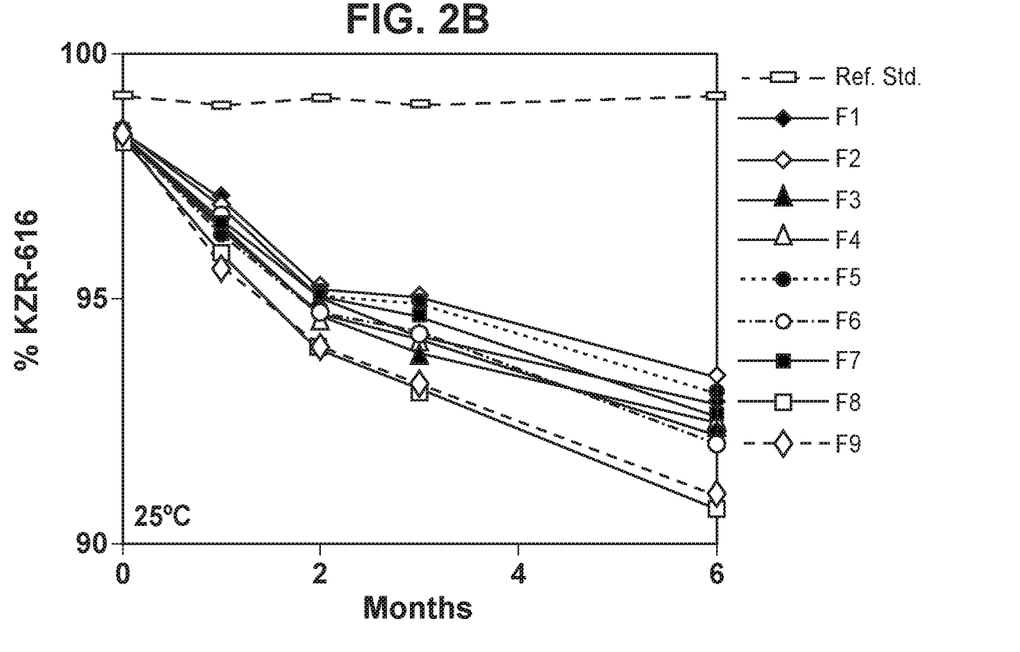
FIG. 2B shows RP-HPLC analysis trends for various formulations after storage for 6 months at 25° C.
Figure 2C:
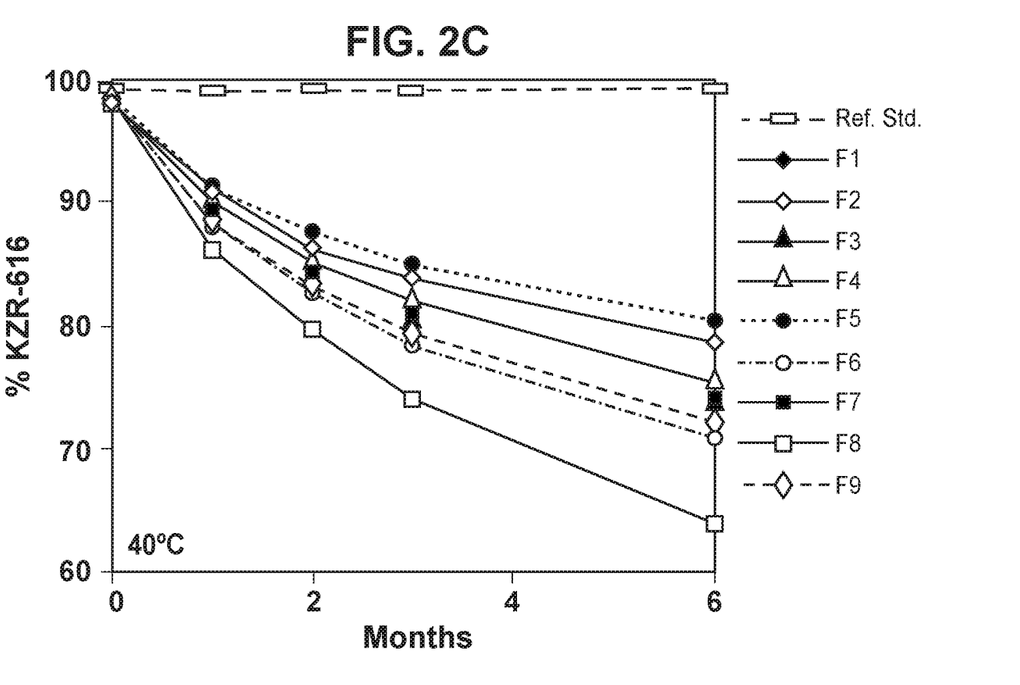
FIG. 2C shows RP-HPLC analysis trends for various formulations after storage for 6 months at 40° C.

Following six (6) months of incubation at 5° C., all reconstituted formulations showed decreases in main peak percentages (97.9%-98.1%), seen in FIG. 1A, compared to those observed at time zero (98.2%-98.4%). Following six (6) months of incubation at 25° C., all reconstituted formulations showed increases in degradant peaks compared to those stored at 5° C. Formulations F2 and F5 showed the highest percentages of KZR-616 (93.4% and 93.1%, respectively) seen in FIG. 1B. Following six (6) months of incubation at 40° C., all reconstituted formulations showed increases in Unknown RRT=0.1 (≤12.5%), KZR-59587 (≤16.1%), Unknown RRT=0.5 (≤1.4%), KZR-0214143 (≤1.9%), and Unknown RRT=2.2 (≤2.4%), seen in FIG. 10, compared to those stored at 5° C. Following 25° C. and 40° C. storage, formulations F2 (unbuffered containing 0.4% mannitol and 1% trehalose at pH 4.2) and F5 (unbuffered containing 2% trehalose at pH 4.2) exhibited the highest main peak percentages among all the candidate formulations. This data suggested that KZR-616 is most stabilized in an unbuffered formulation at pH 4.2 in the presence of sugars (Table 27). This is further supported by the trends of the formulations containing no sugars, F3, F6, and F8, showing the poorest stability results. RP-HPLC data results support formulation F5 as the leading formulation and the best candidate formulation for KZR-616.

TABLE 25

| | RP-HPLC Integration Table (T = 6 Month at 5° C.) | | | | | | | | | |
|---|---|---|---|---|---|---|---|---|---|---|
| KZR-616 | Unknown RRT = 0.1 (%) | KZR-59587 (%) | Unknown RRT = 0.5 (%) | KZR-0214138 (%) | KZR-0214142 (%) | KZR-616 (%) | KZR-0214117 (%) | KZR-0214143 (%) | Unknown RRT = 2.2 (%) | Total Area (mAU) |
| Ref. Std. (Beg.) | 0.2 | 0.2 | 0.1 | 0.0 | 0.1 | 99.2 | 0.1 | 0.1 | 0.1 | 14715.1 |
| F1 | 0.8 | 0.5 | 0.1 | 0.0 | 0.1 | 98.1 | 0.1 | 0.1 | 0.2 | 12681.3 |
| F2 | 0.8 | 0.5 | 0.1 | 0.0 | 0.1 | 98.1 | 0.1 | 0.1 | 0.2 | 13184.2 |
| F3 | 0.8 | 0.5 | 0.1 | 0.0 | 0.1 | 98.0 | 0.1 | 0.2 | 0.2 | 13692.5 |
| F4 | 0.9 | 0.5 | 0.1 | 0.0 | 0.1 | 98.0 | 0.1 | 0.1 | 0.2 | 12171.1 |
| F5 | 0.8 | 0.5 | 0.1 | 0.0 | 0.1 | 98.1 | 0.1 | 0.1 | 0.2 | 12603.6 |
| F6 | 0.8 | 0.5 | 0.1 | 0.0 | 0.1 | 98.0 | 0.1 | 0.1 | 0.2 | 12763.0 |
| F7 | 0.8 | 0.5 | 0.2 | 0.0 | 0.1 | 98.0 | 0.1 | 0.1 | 0.2 | 12544.6 |
| F8 | 0.9 | 0.6 | 0.1 | 0.0 | 0.1 | 97.9 | 0.1 | 0.1 | 0.2 | 14705.2 |
| F9 | 1.0 | 0.5 | 0.1 | 0.0 | 0.1 | 97.9 | 0.1 | 0.1 | 0.2 | 12858.5 |
| Ref. Std. (End) | 0.2 | 0.2 | 0.1 | 0.0 | 0.0 | 99.2 | 0.1 | 0.1 | 0.1 | 14831.6 |

TABLE 26

| | RP-HPLC Integration Table (T = 6 Month at 25° C.) | | | | | | | | | |
|---|---|---|---|---|---|---|---|---|---|---|
| KZR-616 | Unknown RRT = 0.1 (%) | KZR-59587 (%) | Unknown RRT = 0.5 (%) | KZR-0214138 (%) | KZR-0214142 (%) | KZR-616 (%) | KZR-0214117 (%) | KZR-0214143 (%) | Unknown RRT = 2.2 (%) | Total Area (mAU) |
| Ref. Std. (Beg.) | 0.2 | 0.2 | 0.1 | 0.0 | 0.1 | 99.2 | 0.1 | 0.1 | 0.1 | 14715.1 |
| F1 | 3.5 | 2.3 | 0.3 | 0.0 | 0.1 | 92.8 | 0.1 | 0.3 | 0.6 | 12957.6 |
| F2 | 3.3 | 2.0 | 0.4 | 0.0 | 0.1 | 93.4 | 0.1 | 0.3 | 0.5 | 12800.5 |
| F3 | 3.7 | 2.4 | 0.3 | 0.0 | 0.1 | 92.5 | 0.1 | 0.4 | 0.5 | 13328.1 |
| F4 | 3.9 | 2.3 | 0.5 | 0.0 | 0.1 | 92.3 | 0.1 | 0.4 | 0.5 | 13033.0 |
| F5 | 3.4 | 2.0 | 0.5 | 0.0 | 0.1 | 93.1 | 0.1 | 0.3 | 0.5 | 12637.0 |

TABLE 26-continued

RP-HPLC Integration Table (T = 6 Month at 25° C.)

| KZR-616 | Unknown RRT = 0.1 (%) | KZR-59587 (%) | Unknown RRT = 0.5 (%) | KZR-0214138 (%) | KZR-0214142 (%) | KZR-616 (%) | KZR-0214117 (%) | KZR-0214143 (%) | Unknown RRT = 2.2 (%) | Total Area (mAU) |
|---|---|---|---|---|---|---|---|---|---|---|
| F6 | 3.8 | 2.6 | 0.3 | 0.0 | 0.1 | 92.0 | 0.1 | 0.4 | 0.7 | 12645.9 |
| F7 | 3.6 | 2.2 | 0.4 | 0.0 | 0.1 | 92.6 | 0.1 | 0.3 | 0.6 | 12014.0 |
| F8 | 4.4 | 3.3 | 0.4 | 0.0 | 0.1 | 90.7 | 0.1 | 0.4 | 0.7 | 12957.5 |
| F9 | 4.4 | 2.7 | 0.6 | 0.0 | 0.1 | 91.0 | 0.1 | 0.5 | 0.6 | 12081.2 |
| Ref. Std. (End) | 0.2 | 0.2 | 0.1 | 0.0 | 0.0 | 99.2 | 0.1 | 0.1 | 0.1 | 14831.6 |

TABLE 27

RP-HPLC Integration Table (T = 6 Month at 40° C.)

| KZR-616 | Unknown RRT = 0.1 (%) | KZR-59587 (%) | Unknown RRT = 0.5 (%) | KZR-0214138 (%) | KZR-0214142 (%) | KZR-616 (%) | KZR-0214117 (%) | KZR-0214143 (%) | Unknown RRT = 2.2 (%) | Total Area (mAU) |
|---|---|---|---|---|---|---|---|---|---|---|
| Ref. Std. (Beg.) | 0.2 | 0.2 | 0.1 | 0.0 | 0.1 | 99.2 | 0.1 | 0.1 | 0.1 | 14715.1 |
| F1 | 9.1 | 11.2 | 1.3 | 0.1 | 0.2 | 74.8 | 0.1 | 1.3 | 2.0 | 11932.6 |
| F2 | 7.9 | 9.1 | 1.1 | 0.0 | 0.1 | 78.7 | 0.1 | 1.3 | 1.8 | 12320.5 |
| F3 | 9.7 | 11.5 | 1.0 | 0.1 | 0.2 | 74.0 | 0.1 | 1.5 | 2.0 | 12586.1 |
| F4 | 9.1 | 10.6 | 1.5 | 0.1 | 0.1 | 75.4 | 0.1 | 1.5 | 1.8 | 12117.3 |
| F5 | 7.6 | 7.9 | 1.1 | 0.1 | 0.1 | 80.3 | 0.1 | 1.3 | 1.5 | 12636.8 |
| F6 | 10.5 | 13.0 | 1.1 | 0.0 | 0.2 | 70.9 | 0.1 | 1.6 | 2.5 | 13020.1 |
| F7 | 9.0 | 11.3 | 1.2 | 0.0 | 0.1 | 74.2 | 0.1 | 1.5 | 2.5 | 12436.7 |
| F8 | 13.4 | 16.7 | 1.2 | 0.1 | 0.3 | 63.8 | 0.1 | 2.0 | 2.6 | 12248.9 |
| F9 | 10.1 | 12.4 | 1.5 | 0.0 | 0.1 | 72.2 | 0.1 | 1.6 | 2.0 | 13014.8 |
| Ref. Std. (End) | 0.2 | 0.2 | 0.1 | 0.0 | 0.0 | 99.2 | 0.1 | 0.1 | 0.1 | 14831.6 |

Following six (6) months of incubation at 5° C., all formulations showed slight changes in main peak percentages. However, all formulations still retained main peak percentages of ≥97.9%. Following six (6) months of incubation at 25° C., all formulations retained main peak percentages ≥90.7%. Formulations F2 and F5 showed the highest main peak percentages and the slowest rate of degradation. Following six (6) months of incubation at 40° C., all formulations, with the exception of F8, retained main peak percentages of ≥70.0%. Formulation F5 showed the highest main peak percentages and the slowest rate of degradation (80.3%).

Moisture Optimization

The objective of this study was to determine if a modified lyophilization cycle could further improve the stability of KZR-616 during refrigerated storage. This lyophilization cycle optimization study focused on the leading formulation (2% trehalose, pH 4.2) from the previous study. Leading formulation F5 was prepared with drug substances from Lot A (015072369-FF16001) and Lot B (1605R110). Varying drug substance lots were lyophilized using different secondary drying temperatures to achieve optimum moisture content (Table 5).

Visual Analysis

At time zero, all Pre-lyophilization samples were visually clear, free of particles and displayed a yellowish coloration. The fresher drug substance (Lot B) displayed a lighter coloration compared to drug substance (Lot A). Following lyophilization, all samples displayed elegant cakes. Following 4 weeks at 40° C., samples displayed comparable clarity and coloration to time zero.

pH Measurements

All reconstituted samples at T=4 Week displayed comparable pH values (Table 28). Slight increases were observed compared to time zero (≥±0.19).

TABLE 28

Moisture Opt. pH (Time Zero & T = 4 Week)

| | pH | | |
|---|---|---|---|
| | T = 0 | | |
| Sample Code | Pre-lyophilization | Reconstituted | T = 4 Week Reconstituted |
| 10A | 4.18 | 4.16 | 4.31 |
| 25A | 4.19 | 4.18 | 4.31 |
| 35A | 4.19 | 4.16 | 4.32 |
| 50A | 4.19 | 4.20 | 4.36 |
| 25B | 4.22 | 4.22 | 4.41 |

Concentration Measurements

Following four (4) weeks of incubation at 40° C., all samples showed similar concentration values compared to time zero (Ta

TABLE 29

Moisture Opt. Concentration (Time Zero & T = 4 week)

| | T = 0 | | |
|---|---|---|---|
| Sample Code | Pre-lyophilization | Reconstituted | T = 4 Week Reconstituted |
| 10A | 150 | 139 | 140 |
| 25A | 150 | 132 | 138 |
| 35A | 150 | 138 | 138 |
| 50A | 150 | 137 | 140 |
| 25B | 147 | 131 | 134 |

Reconstitution Time Measurements

Following lyophilization at varying secondary drying temperatures, formulations were reconstituted with one milliliter of filtered MQ. Upon the addition of MQ, a timer was started to measure the amount of time each formulation required to homogenize. Following four (4) weeks of incubation at 40° C., all samples showed reconstitution times of <4 minutes; 35 A displayed the shortest reconstitution times of 2 minutes and 15 seconds; sample 10 A displayed the longest reconstitution time of 3 minutes and 35 seconds (Table 30).

TABLE 30

Moisture Opt. Reconstitution Time (Time Zero & 4 weeks)

| Sample Code | Reconstitution Time (min) Time Zero | Reconstitution Time (min) T = 4 weeks |
|---|---|---|
| 10A | 6:59 | 3:35 |
| 25A | 3:50 | 2:58 |
| 35A | 5:50 | 2:15 |
| 50A | 4:22 | 3:16 |
| 25B | 3:27 | 3:06 |

Moisture Content Measurements (Karl Fischer)

Following 6 months of incubation, formulations displayed comparable moisture content values to time zero (Table 31). All lyophilized formulations continued to show moisture content values less than 1%. The difference in secondary drying temperatures displayed a slight difference in moisture content; higher temperatures displayed the least moisture percentages.

TABLE 31

Moisture Opt. Moisture Content Measurements (Time Zero)

| Sample Code | % Moisture Content | % Average |
|---|---|---|
| 1% Water Std | 0.92 | |
| 10A #1 | 0.24 | 0.34 |
| 10A #2 | 0.40 | |
| 10A #3 | 0.39 | |
| 25A #1 | 0.36 | 0.32 |
| 25A #2 | 0.29 | |
| 25A #3 | 0.30 | |
| 35A #1 | 0.17 | 0.21 |
| 35A #2 | 0.20 | |
| 35A #3 | 0.27 | |
| 50A #1 | 0.20 | 0.19 |
| 50A #2 | 0.19 | |
| 50A #3 | 0.18 | |
| 25B #1 | 0.29 | 0.31 |
| 25B #2 | 0.33 | |

RP-HPLC Analysis

Following four (4) weeks of incubation at 40° C., all reconstituted formulations showed decreases in main peak percentages (90.3%-91.7%) compared to those observed at time zero (97.7%-98.6%). RP-HPLC identified the main degradant species in the KZR-616 molecule. Peaks RRT=0.1, KZR-59587, KZR-0214143 and RRT=2.2 displayed the highest increase in peak percentages when stressed. The difference in secondary drying temperatures displayed a slight difference in main peak stability at time zero. Following four weeks at 40° C., all samples displayed comparable stability.

The samples from Lot B showed larger decreases in main peak percentages compared to the corresponding Lot A samples, with a main peak percentage of 90.3%. This was due to large increases in KZR-0214142 that were observed in addition to the degradant peaks not observed in samples from Lot A.

TABLE 32

Moisture Opt. RP-HPLC Integration Table (Time Zero)

| KZR-616 | Unknown RRT = 0.1 (%) | KZR-59587 (%) | Unknown RRT = 0.5 (%) | KZR-0214138 (%) | KZR-0214142 (%) | KZR-616 (%) | KZR-0214117 (%) | KZR-0214143 (%) | Unknown RRT = 2.2 (%) | Total Area (mAU) |
|---|---|---|---|---|---|---|---|---|---|---|
| Ref. Std. (Beg.) | 0.2 | 0.3 | 0.1 | 0.0 | 0.0 | 99.1 | 0.0 | 0.1 | 0.1 | 15234 |
| 10A, T = 0 | 0.3 | 0.5 | 0.1 | 0.0 | 0.1 | 98.5 | 0.1 | 0.3 | 0.2 | 12202 |
| 25A, T = 0 | 0.4 | 0.5 | 0.0 | 0.0 | 0.1 | 98.5 | 0.1 | 0.3 | 0.2 | 12314 |
| 35A, T = 0 | 0.6 | 0.5 | 0.1 | 0.0 | 0.1 | 98.2 | 0.1 | 0.3 | 0.2 | 12396 |
| 50A, T = 0 | 1.0 | 0.6 | 0.2 | 0.0 | 0.1 | 97.7 | 0.1 | 0.2 | 0.2 | 12697 |
| 25B, T = 0 | 0.4 | 0.3 | 0.1 | 0.1 | 0.1 | 98.6 | 0.0 | 0.3 | 0.1 | 12057 |
| Ref. Std. (End) | 0.2 | 0.3 | 0.1 | 0.0 | 0.1 | 99.1 | 0.0 | 0.2 | 0.1 | 15005 |

TABLE 33

Moisture Opt. RP-HPLC Integration Table (T = 4 week)

| KZR-616 | Unknown RRT = 0.1 (%) | KZR-59587 (%) | Unknown RRT = 0.5 (%) | KZR-0214138 (%) | KZR-0214142 (%) | KZR-616 (%) | KZR-0214117 (%) | KZR-0214143 (%) | Unknown RRT = 2.2 (%) | Total Area (mAU) |
|---|---|---|---|---|---|---|---|---|---|---|
| Ref. Std. (Beg.) | 0.1 | 0.3 | 0.1 | 0.0 | 0.0 | 99.1 | 0.1 | 0.1 | 0.1 | 15237 |
| 10A, T = 4 wk | 4.2 | 2.4 | 0.7 | 0.0 | 0.2 | 91.5 | 0.1 | 0.4 | 0.6 | 13770 |
| 25A, T = 4 wk | 4.0 | 2.4 | 0.8 | 0.0 | 0.2 | 91.6 | 0.1 | 0.5 | 0.5 | 12388 |
| 35A, T = 4 wk | 4.1 | 2.3 | 0.9 | 0.0 | 0.2 | 91.5 | 0.1 | 0.4 | 0.5 | 11925 |
| 50A, T = 4 wk | 3.9 | 2.3 | 0.9 | 0.0 | 0.2 | 91.7 | 0.1 | 0.5 | 0.5 | 12174 |
| 25B, T = 4 wk | 4.1 | 2.3 | 1.2 | 0.1 | 1.1 | 90.3 | 0.0 | 0.4 | 0.6 | 11745 |
| Ref. Std. (End) | 0.2 | 0.3 | 0.1 | 0.0 | 0.0 | 99.2 | 0.0 | 0.1 | 0.1 | 15199 |

RP-HPLC displayed the degradant species increases after four weeks at 40° C. Lot B displayed an additional peak (~10 min), that was not present in Lot A samples.

The stability of KZR-616 in various formulation conditions was examined in this Lyophilization Formulation Development study. The conditions investigated in this study included buffered (10 mM succinate) and unbuffered formulations with various bulking agents (L-Glycine, Mannitol, Trehalose) at different pH values (3.9-4.2). The stability of KZR-616 in different formulations was examined under storage conditions at refrigerated (5° C.), ambient (25° C.), and accelerated (40° C.) temperatures for up to 6 months and was analyzed by Reversed Phase HPLC (RP-HPLC) to evaluate KZR-616 stability.

Prior to the initiation of the Accelerated Stability Study, two rounds of lyophilization cycle development were performed. Both development cycles displayed elegant cakes and post reconstitution samples that were visually free of particles and slightly yellow in coloration. Lyophilization cycle #1 displayed good stability by RP-HPLC. However, after measuring pH and osmolality, the results displayed off-target pH and osmolality values. Lyophilization cycle #2 was performed on formulations with optimized bulking agents to achieve target pH and osmolality. Furthermore, cycle 2 decreased the loading phase, increased the primary drying shelf temperature, and decreased the secondary drying shelf temperature. Samples generated by Cycle #2 displayed an elegant cake and good stability by RP-HPLC.

Upon storage over 6 months, lyophilized formulations consistently displayed elegant cakes at all storage temperatures. However, lyophiles displayed an increase in yellow coloration, especially when stored at 25° C. and 40° C., and became more apparent after reconstitution. Following reconstitution, all formulations were free of particles. No significant changes in pH or concentration were observed over time. Reconstitution time was consistently less than four minutes and thirty seconds for all formulations over 6 months of storage, regardless of storage temperature.

The chemical stability assessment of all formulations at all storage temperatures was performed using RP-HPLC. Following 6 months of storage at 5° C., formulations displayed comparable main peak percentages to time zero (98.2%-98.4%), retaining main peak percentages 97.9%. Following 6 months of storage at 25° C., formulations displayed decreased main peak percentages compared to time zero (98.2%-98.4%), retaining main peak (KZR-616) percentages (90.7% to 93.4%). Trehalose-containing formulations F1, F2 and F5 displayed the highest main peak percentages (92.8%, 93.4%, and 93.1%) after 6 months at 25° C. Following 6 months of storage at 40° C., formulations displayed a significant decrease in main peak percentages compared to time zero (98.2%-98.4%), retaining main peak (KZR-616) percentages (63.8% to 80.3%).

An additional moisture optimization study was performed on leading formulation F5 to optimize the lyophilization cycle, decrease the moisture content, and greater improve KZR-616 stability. The moisture optimization study performed lyophilization cycles with various secondary shelf temperatures of 10° C., 25° C., 35° C. and 50° C.

After 4 weeks of storage at 40° C., all samples from lot C15072369-FF16001 showed comparable visual appearance, pH, concentration, reconstitution times, and peak percentages by RP-HPLC, regardless of secondary drying shelf temperature. Following 4 weeks of incubation at 40° C., all reconstituted formulations from lot C15072369-FF16001 showed decreases in main peak percentages (91.5%-91.7%) compared to those observed at time zero (97.7%-98.6%). Utilizing RP-HPLC, the main degradant species in the KZR-616 molecule were identified. Peaks RRT=0.1, KZR-59587, KZR-0214143 and RRT=2.2 displayed the highest increase in peak percentages when stressed. The sample from lot 1605R110 showed larger decreases in main peak percentages compared to the corresponding lot 015072369-FF16001 sample, with a main peak percentage of 90.3%. This was due to large increases in KZR-0214142 that were observed in addition to the degradant peaks observed in samples from lot 015072369-FF16001. This study yielded comparable KZR-616 stability after 4 weeks and confirmed low moisture content values, with no significant moisture difference between lyophilization cycles. The difference in secondary drying temperatures displayed a slight difference in main peak stability at time zero. Following four weeks at 40° C., all formulated samples displayed comparable stability, suggesting that improved stability was not achieved with further drying of the cake.

In conclusion, trehalose-containing formulations F2 and F5 displayed the highest main peak percentages (78.7%, 80.3%) after 6 months at 40° C. This data suggests that KZR-616 is most stabilized in an unbuffered formulation at pH 4.2 in the presence of sugars. This is further supported by the trends of sugar-free formulations F3, F6, and F8 showing the poorest stability results.

Example 2

Tables 34-36 show a comparison of the pharmacokinetics ("PK") and toxicokinetics ("TK") observed with different KZR-616 formulations in various animals. The Test Formulation comprises various concentrations of KZR-616 as noted in 2 wt % trehalose at pH 4.2 upon dissolution with water for injection. The Comparative Formulation comprises various concentrations of KZR-616 as noted in aqueous 10 wt % polysorbate-80 ("PS-80").

Table 34 shows that the Test Formulation exhibited faster absorption and elimination as well as 2-3 fold higher $C_{max}$ compared to the Comparative formulation. Similar AUCs were observed for both formulations.

TABLE 34

Monkey TK Comparison

| | | | Comparative | | | | Test | | | |
|---|---|---|---|---|---|---|---|---|---|---|
| Day | Dose (mg/kg) | Sex | $T_{1/2}$ (hr) | $T_{max}$ (hr) | $C_{max}$ (ng/mL) | $AUC_{0-6}$ (ng * hr/mL) | $T_{1/2}$ (hr) | $T_{max}$ (hr) | $C_{max}$ (ng/mL) | $AUC_{0-24}$ (ng * hr/mL) |
| 1 | 1.0 | M | 0.45 | 0.27 | 211 | 197 | 0.15 | 0.10 | 512 | 199 |
| | | F | 0.56 | 0.38 | 190 | 226 | 0.14 | 0.10 | 534 | 197 |
| | 2.0 | M | 0.53 | 0.27 | 388 | 425 | 0.17 | 0.10 | 1124 | 439 |
| | | F | 0.58 | 0.36 | 358 | 402 | 0.16 | 0.12 | 902 | 346 |

TABLE 34-continued

Monkey TK Comparison

| | | | | Comparative | | | | Test | | |
|---|---|---|---|---|---|---|---|---|---|---|
| Day | Dose (mg/kg) | Sex | $T_{1/2}$ (hr) | $T_{max}$ (hr) | $C_{max}$ (ng/mL) | $AUC_{0-6}$ (ng * hr/mL) | $T_{1/2}$ (hr) | $T_{max}$ (hr) | $C_{max}$ (ng/mL) | $AUC_{0-24}$ (ng * hr/mL) |
| | 4.0 | M | 0.50 | 0.21 | 841 | 775 | 0.18 | 0.10 | 2533 | 767 |
| | | F | 0.56 | 0.30 | 742 | 796 | 0.16 | 0.12 | 2012 | 766 |

Table 35 shows faster absorption and elimination as well as 1.2-3.7 fold higher $C_{max}$ was observed for the Test formulation. A 0.7-1.7 fold difference in AUCs was observed for the two formulations.

TABLE 35

Rat TK Comparison

| Test | | | | | Comparative | | | |
|---|---|---|---|---|---|---|---|---|
| Dose (mg/kg) | $T_{1/2}$ (hr) | $T_{max}$ (hr) | $C_{max}$ (ng/mL) | $AUC_{0-24}$ (ng * hr/mL) | $T_{1/2}$ (hr) | $T_{max}$ (hr) | $C_{max}$ (ng/mL) | $AUC_{0-6}$ (ng * hr/mL) |
| 0.75 D7 | NA | 0.25 | 245 | 128 | 0.60 | 0.50 | 138 | 179 |
| 0.75 D17 | 0.19 | 0.25 | 359 | 239 | 0.62 | 0.50 | 98.0 | 150 |
| 1.5 D7 | 0.19 | 0.25 | 418 | 277 | 0.65 | 0.50 | 297 | 346 |
| 1.5 D17 | 0.24 | 0.25 | 518 | 457 | 0.65 | 0.50 | 163 | 272 |
| 3.0 D7 | 0.22 | 0.25 | 639 | 464 | 0.83 | 0.50 | 544 | 790 |
| 3.0 D17 | 0.23 | 0.25 | 966 | 893 | 0.83 | 0.50 | 483 | 712 |

The Test Formulation of Table 36 was prepared as a water for injection ("WFI") formulation described above and Comparative Formulation was prepared as an aqueous 10 wt % polysorbate-80 ("PS-80") formulation. Faster absorption and elimination as well as 1.1-2.4 fold higher $C_{max}$ was observed for the Test formulation. A 0.6-1.0 fold difference in AUCs was observed for the two formulations.

TABLE 36

Rabbit TK Comparison

| Test | | | | | Comparative | | | |
|---|---|---|---|---|---|---|---|---|
| Dose (mg/kg) | $T_{1/2}$ (hr) | $T_{max}$ (hr) | $C_{max}$ (ng/mL) | $AUC_{0-24}$ (ng * hr/mL) | $T_{1/2}$ (hr) | $T_{max}$ (hr) | $C_{max}$ (ng/mL) | $AUC_{0-6}$ (ng * hr/mL) |
| 0.3 DG7 | NA | 0.28 | 64.9 | 39.8 | 0.87 | 1.00 | 35.8 | 66.8 |
| 0.3 DG19 | NA | 0.25 | 86.6 | 53.5 | 0.67 | 0.50 | 47.3 | 62.7 |
| 0.6 DG7 | NA | 0.33 | 130 | 86.7 | 1.45 | 0.50 | 59.7 | 113 |
| 0.6 DG19 | 0.34 | 0.28 | 156 | 127 | 0.85 | 0.25 | 145 | 153 |
| 1.2 DG7 | 0.28 | 0.19 | 313 | 231 | 0.97 | 0.25 | 131 | 233 |
| 1.2 DG19 | 0.31 | 0.42 | 310 | 236 | 1.12 | 0.25 | 254 | 339 |

What is claimed:
1. A pharmaceutical formulation comprising KZR-616 maleate salt, and a sugar comprising trehalose, wherein KZR-616 has a structure and the formulation is a lyophilized formulation that upon reconstitution, has a pH of 3.8 to 4.3 and a concentration of 1.5 wt % to 5 wt % trehalose.

2. The formulation of claim 1, having a pH of 4.2.

3. The formulation of claim 1, absent an additional buffer.

4. The formulation of claim 1, wherein the KZR-616 maleate salt is present at an amount of 100 to 200 mg/mL, as measured prior to lyophilization, based upon the weight of the KZR-616 free base.

5. The formulation of claim 4, wherein the KZR-616 maleate salt is present in an amount of 125 mg/mL based on the weight of the KZR-616 free base.

6. The formulation of claim 1, wherein the trehalose is present in an amount of 2 wt %.

7. The formulation of claim 1, wherein the sugar further comprises mannitol.

8. The formulation of claim 1, having a pH of 4.1 to 4.3 (as measured when reconstituted) after storage at 5° C., 25° C., or 40° C. for at least six months.

9. The formulation of claim 1, having a concentration of KZR-616 maleate salt of 140 mg/mL to 150 mg/ml (as measured when reconstituted) after storage at 5° C., 25° C., or 40° C. for at least six months.

10. The formulation of claim 1, having a reconstitution time of less than 4.5 minutes after storage at 5° C., 25° C., or 40° C. for at least six months.

11. The formulation of claim 1, wherein the lyophilized formulation has a moisture content of less than 1% after storage at 5° C., 25° C., or 40° C. for at least six months.

12. The formulation of claim 1, wherein the KZR-616 maleate salt is at least 93% pure after storage at 5° C., 25° C., or 40° C. for at least six months.

13. A reconstituted formulation comprising the formulation of claim 1 and a solvent for reconstitution, wherein the solvent for reconstitution comprises water for injection (WFI) or aqueous 5% dextrose, and the reconstituted formulation has an osmolality of 275 to 325 mOsm.

14. The reconstituted formulation of claim 13, having an absorption rate, as measured by $T_{1/2}$, of at least 50% faster than that of a formulation comprising KZR-616 maleate salt and polysorbate-80.

15. The reconstituted formulation of claim 13, having a $C_{max}$ of at least 150% that of a formulation comprising KZR-616 maleate salt and polysorbate-80 ("PS-80 formulation").

16. A method of treating an immune-related disease or inflammation in a subject comprising administering the reconstituted formulation of claim 13.

* * * * *